US005639869A

United States Patent [19]

Cole et al.

[11] Patent Number: 5,639,869

[45] Date of Patent: Jun. 17, 1997

[54] MYCOPLASMA ARTHRITIDIS T-CELL MITOGEN

[75] Inventors: Barry C. Cole, Sandy; Curtis L. Atkin, Salt Lake City, both of Utah; Arnold R. Oliphant, Johnston, Iowa; Ann Pole, Salt Lake City, Utah

[73] Assignee: University of Utah, Salt Lake City, Utah

[21] Appl. No.: 165,038

[22] Filed: Dec. 10, 1993

[51] Int. Cl.$^6$ .......... C07H 21/04

[52] U.S. Cl. .......... 536/23.7; 530/350; 530/326; 530/825; 424/264.1

[58] Field of Search .......... 530/350, 326, 530/825; 424/264.1

[56] References Cited

PUBLICATIONS

Hartwig et al, International Immunology 5(8): 869–875, 1993.
Komisar et al, Infect & Immunity 62(11): 4775–4780, 1994.
Kuppler et al, J. Exp. Med 175: 387–396, 1992.
Kotzin et al, Advances in Immunology 54: 99–166, 1993..
Atkin et al, Abstracts Annu. Meet. American Society Microbiol 90: 139, 1990.
Cole B.C. Curr. Topics. Micro Immunol 174:107–119, 1991.
Cole et al, Immunology Today 12(8): 271–276, 1991.
Webb et al, Curr. Opinion. Immunol. 6:467–475, 1994.
Adorini et al, Springer Semin. Immunopathol. 14:187–199 1992.

*Primary Examiner*—James C. Housel
*Assistant Examiner*—Bao-Thuy L. Nguyen
*Attorney, Agent, or Firm*—Thorpe, North & Western, L.L.P.

[57] ABSTRACT

A method of purifying *Mycoplasma arthritidis* mitogen (MAM) to electrophoretic and sequence homogeneity is disclosed. A preparation of MAM purified according to this method was used to determine the sequence of the N-terminal 54 amino acids of MAM. A synthetic peptide consisting of amino acids 15–32 inhibited MAM-induced cell proliferation in vitro. The sequence of the N-terminal 54 amino acids was reverse translated, nucleotide probes were designed therefrom, and the MAM gene was selected from a genomic library. The MAM gene was sequenced and found to be contained on a 1107 bp DNA fragment. The primary translation product contains a 39 amino acid signal sequence and a 213 amino acid mature MAM (molecular weight 25,294). Amino acid sequence comparisons of MAM to bacterial and murine tumor virus superantigens showed regions of conservative sequence homology, including the region capable of inhibiting cell proliferation. Sequence homologies to HIV and other retrovirus proteins and to certain regulatory proteins were also detected. Strategies for blocking or immunizing against certain diseases, including autoimmune diseases, are disclosed.

4 Claims, 8 Drawing Sheets

| | 1 | | | | 5 | | | | | 10 | | | | | 15 | | | | | 20 | | | | | 25 | | |
|---|---|---|---|---|---|---|---|---|---|---|---|---|---|---|---|---|---|---|---|---|---|---|---|---|---|---|---|
| SEQ ID NO: 8 | Gln | Lys | His | Phe | Val | Gln | Asn | Leu | Asn | Asn | Val | Val | Phe | Thr | Asn | Lys | Glu | Leu | Glu | Asp | Ile | Tyr | Asn | Leu | Ser | Asn | Lys |
| SEQ ID NO: 9 | Lys | Ser | Ile | Asp | Gln | Phe | Leu | Tyr | Phe | Asp | Leu | Ile | Tyr | Ser | Ile | Lys | Asp | Thr | Lys | Leu | Gly | Asn | Tyr | Asp | Asn | Val | Arg |
| SEQ ID NO: 10 | Thr | Lys | Leu | Gly | Asn | Tyr | Asp | Asn | Val | Arg | Val | Glu | Phe | Lys | Asn | Lys | Asp | Leu | Ala | Asp | Lys | Tyr | Lys | Asp | Lys | Tyr | Val |
| SEQ ID NO: 11 | Asp | His | Tyr | Val | Ser | Ala | Thr | Lys | Val | Lys | Ser | Val | Asp | Lys | Phe | Leu | Ala | His | Asp | Leu | Ile | Tyr | Asn | Ile | Ser | Asp | Lys |
| SEQ ID NO: 12 | Asn | His | Phe | Asp | Asn | Gly | Asn | Leu | Gln | Asn | Val | Leu | Ile | Arg | Val | Tyr | Glu | Asn | Lys | Arg | Asn | Thr | Ile | Ser | Phe | Glu | Val |
| SEQ ID NO: 13 | Asp | Asn | Gly | Asn | Leu | Gln | Asn | Val | Leu | Ile | Arg | Val | Tyr | Glu | Asn | Lys | Arg | Asn | Thr | Ile | Ser | Phe | Glu | Val | Gln | Thr | Asp |
| SEQ ID NO: 14 | Ser | Gly | Glu | Ser | Gln | Gln | Asn | Leu | Asn | Asn | Lys | Ile | Ile | Leu | Glu | Lys | Asp | Ile | Val | Thr | Phe | Gln | Glu | Ile | Asp | Phe | Lys |
| SEQ ID NO: 7 | | | | Phe | Val | Gln | Asn | Leu | Asn | Asn | Val | Val | Phe | Thr | Asn | Lys | Glu | Leu | Glu | Asp | Ile | Cys | | | | | |

Fig. 6

| SEQ ID | 1 | | | | 5 | | | | | | 10 | | | | | | 15 | | | | | 20 | | | | | 25 | |
|---|---|---|---|---|---|---|---|---|---|---|---|---|---|---|---|---|---|---|---|---|---|---|---|---|---|---|---|---|
| NO: 16 | Lys | Ala | Gln | Lys | His | Phe | Val | Gln | --- | --- | Asn | Leu | Asn | Asn | Val | Val | Phe | Thr | Asn | Lys | Glu | Leu | Glu | Asp | Ile | Tyr | Asn | Leu |
| NO: 17 | Ser | Phe | Asn | Ser | Ser | Ser | Val | Gln | Asp | Tyr | Asn | Leu | Asn | Asn | Ser | Glu | Asn | Ser | Thr | Phe | Leu | Leu | Gly | Gln | Gly | Pro | Gln | Pro |
| NO: 18 | Pro | Ser | Glu | Ile | Glu | Ile | Arg | Met | --- | --- | Leu | Ala | Lys | Asn | Tyr | Ile | Phe | Thr | Asn | Lys | Thr | Asn | Pro | Ile | Gly | Arg | Leu | Leu |
| NO: 19 | Arg | Pro | Arg | Gly | Lys | Lys | Arg | Tyr | --- | --- | Lys | Leu | Lys | His | Ile | Val | Trp | Ala | Ser | Arg | Glu | Leu | Glu | Arg | Phe | Ala | Val | Asn |
| NO: 20 | Ser | Gln | Asn | Tyr | Pro | Ile | Val | Gln | --- | --- | Asn | Leu | Gln | Gly | Gln | Met | Val | His | Gln | Ala | Ile | Ser | Pro | Arg | Thr | Leu | Asn | Ala |
| NO:21 | Arg | Leu | Leu | Ser | Gly | Ile | Val | Gln | --- | --- | Gln | Gln | Asn | Asn | Leu | Leu | Arg | Ala | Ile | Glu | Ala | Gln | Gln | His | Leu | Leu | Lys | Leu |
| NO: 22 | Gly | Lys | Ile | Ile | Cys | Pro | Thr | Asn | --- | --- | Val | Pro | Trp | Asn | Ser | Ser | Trp | Ser | Asn | Lys | Ser | Gln | Ser | Asp | Ile | Trp | Asp | Lys |
| NO: 23 | Leu | Glu | Trp | Asp | Lys | Glu | Val | Ser | --- | --- | Asn | Tyr | Thr | Gln | Val | Ile | Tyr | Asn | Leu | Ile | Glu | Glu | Ser | Gln | Thr | Gln | Gln | Glu |

Fig. 7

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
( A ) LENGTH: 54 amino acids
( B ) TYPE: amino acid
( D ) TOPOLOGY: linear ( i i ) MOLECULE TYPE: protein ( i i i ) HYPOTHETICAL: no ( i v ) ANTI-SENSE: no ( v ) FRAGMENT TYPE: N-terminal fragment ( v i ) ORIGINAL SOURCE:
( A ) ORGANISM: Mycoplasma arthritidis
( B ) STRAIN: PG6
( G ) CELL TYPE: unicellular organism ( i x ) FEATURE:
( A ) NAME/KEY: N-terminal region of mature protein
( B ) LOCATION: 1 to 54
( C ) IDENTIFICATION METHOD: direct sequencing of protein
( D ) OTHER INFORMATION: contains domain that blocks cell proliferation ( x i ) SEQUENCE DESCRIPTION: SEQ ID NO:1:

```
Met Lys Leu Arg Val Glu Asn Pro Lys Lys Ala Gln Lys His Phe Val
  1                 5                  10                  15

Gln Asn Leu Asn Asn Val Val Phe Thr Asn Lys Glu Leu Glu Asp Ile
             20                  25                  30

Tyr Asn Leu Ser Asn Lys Glu Glu Thr Lys Glu Val Leu Lys Leu Phe
         35                  40                  45

Lys Leu Lys Val Xaa Gln
     50
```

( 2 ) INFORMATION FOR SEQ ID NO:2:

( i ) SEQUENCE CHARACTERISTICS:
( A ) LENGTH: 26
( B ) TYPE: nucleic acid
( C ) STRANDEDNESS: single
( D ) TOPOLOGY: linear ( i i i ) HYPOTHETICAL: yes ( i v ) ANTI-SENSE: no -continued ( v i ) ORIGINAL SOURCE:
( A ) ORGANISM: Mycoplasma arthritidis
( B ) STRAIN: PG6
( G ) CELL TYPE: unicellular organism ( x i ) SEQUENCE DESCRIPTION: SEQ ID NO:2:

```
GAAAAYCCAA AAAAAGCWCA AAAACA   26
```

( 2 ) INFORMATION FOR SEQ ID NO:3:

( i ) SEQUENCE CHARACTERISTICS:
( A ) LENGTH: 1107
( B ) TYPE: nucleic acid
( C ) STRANDEDNESS: double
( D ) TOPOLOGY: linear ( i i ) MOLECULE TYPE: genomic DNA ( i i i ) HYPOTHETICAL: no ( i v ) ANTI-SENSE: no ( v i ) ORIGINAL SOURCE:
( A ) ORGANISM: Mycoplasma arthritidis
( B ) STRAIN: PG6
( G ) CELL TYPE: unicellular organism ( x i ) SEQUENCE DESCRIPTION: SEQ ID NO:3:

```
TTTAACACTT CTTTCGGTTA TTAATAACTT TAAATTCTAA TTAAATTGGT AAAGCGGGTA     60

AACAAAGAAA CTATTTAAAA ATTTATGAAA TTAATATTTA ACTTTATAAA ATAAAATTTC    120

GCTGTGAAA ATG AAA TTC TTC ACA AAT TTA AAA ATC ATA AGG AAT AAA AAA    171
          Met Lys Phe Phe Thr Asn Leu Lys Ile Ile Arg Asn Lys Lys
                          -35                 -30

ATG AAA ACA AAA AAA TTA TTA ATC GCA ACC GTC ACT TTA GCG ACT GGG      219
Met Lys Thr Lys Lys Leu Leu Ile Ala Thr Val Thr Leu Ala Thr Gly
-25                 -20                 -15                 -10

CTT TTA GGA ATT TTA CCA TTA ACT AGC ATG AAA CTT AGA GTT GAA AAT      267
Leu Leu Gly Ile Leu Pro Leu Thr Ser Met Lys Leu Arg Val Glu Asn
                -5                   1               5

CCT AAA AAA GCT CAA AAG CAT TTT GTG CAA AAT TTA AAT AAT GTT GTA      315
Pro Lys Lys Ala Gln Lys His Phe Val Gln Asn Leu Asn Asn Val Val
        10                  15                  20

TTT ACT AAT AAA GAG CTT GAA GAT ATC TAC AAT TTA AGT AAT AAA GAA      363
Phe Thr Asn Lys Glu Leu Glu Asp Ile Tyr Asn Leu Ser Asn Lys Glu
    25                  30                  35

GAA ACA AAA GAA GTA TTA AAA TTG TTT AAA TTG AAG GTC AAC CAA TTT      411
Glu Thr Lys Glu Val Leu Lys Leu Phe Lys Leu Lys Val Asn Gln Phe
40                  45                  50                  55

TAT AGA CAT GCT TTT GGT ATA GTG AAT GAC TAC AAT GGA CTT CTT GAA      459
Tyr Arg His Ala Phe Gly Ile Val Asn Asp Tyr Asn Gly Leu Leu Glu
                60                  65                  70

TAC AAA GAA ATT TTT AAT ATG ATG TTT TTA AAA TTA AGC GTT GTC TTT      507
Tyr Lys Glu Ile Phe Asn Met Met Phe Leu Lys Leu Ser Val Val Phe
            75                  80                  85

GAC ACA CAA CGT AAA GAG GCA AAT AAC GTC GAA CAA ATC AAA AGA AAT      555
Asp Thr Gln Arg Lys Glu Ala Asn Asn Val Glu Gln Ile Lys Arg Asn
        90                  95                  100

ATC GCT ATT TTA GAT GAA ATA ATG GCA AAA GCA GAT AAC GAT TTA TCT      603
Ile Ala Ile Leu Asp Glu Ile Met Ala Lys Ala Asp Asn Asp Leu Ser
    105                 110                 115

TAC TTT ATA TCT CAG AAT AAG AAT TTT CAA GAG TTA TGA GAT AAA GCT      651
Tyr Phe Ile Ser Gln Asn Lys Asn Phe Gln Glu Leu Trp Asp Lys Ala
120                 125                 130                 135
```

-continued

```
GTC AAA CTA ACT AAA GAA ATG AAA ATA AAA CTT AAA TTC CAA AAA CTA    699
Val Lys Leu Thr Lys Glu Met Lys Ile Lys Leu Lys Gly Gln Lys Leu
                140                 145                 150

GAT CTT CGT GAT GGT GAA GTT GCA ATA AAC AAA GTA AGA GAA TTA TTT    747
Asp Leu Arg Asp Gly Glu Val Ala Ile Asn Lys Val Arg Glu Leu Phe
            155                 160                 165

GGC AGC GAC AAA AAT GTA AAA GAG CTT TGA TGA TTT AGA TCT CTT CTA    795
Gly Ser Asp Lys Asn Val Lys Glu Leu Trp Trp Phe Arg Ser Leu Leu
        170                 175                 180

GTA AAA GGT GTT TAC CTT ATA AAA CGC TAT TAC GAA GGT GAT ATT GAA    843
Val Lys Gly Val Tyr Leu Ile Lys Arg Tyr Tyr Glu Gly Asp Ile Glu
    185                 190                 195

CTT AAA ACG ACA TCG GAT TTT GCA AAA GCT GTT TTT GAA GAT            885
Leu Lys Thr Thr Ser Asp Phe Ala Lys Ala Val Phe Glu Asp
200                 205                 210

TAATATTAAA CATATATAAC AAATTATCCC CCCAATCTAA AAGGTTGGGG GGATTTTAAA    945

TAAATTCCTT GCATCTAGCA AGGATAAATA AGATAGAAAT AAATTGGTTA GTTAAAAAAT   1005

GTTTGGTCCG TTGCAATTAT GATTTTTTCG TTTTGTATTG TAATTGGCAC TTCGCTATAT   1065

TCCTTTATTT TTCCAGAAAT AATTTCCATA GCAAGCATGT TT                      1107
```

( 2 ) INFORMATION FOR SEQ ID NO:4:

( i ) SEQUENCE CHARACTERISTICS:
( A ) LENGTH: 213 amino acids
( B ) TYPE: amino acid
( D ) TOPOLOGY: linear ( i i ) MOLECULE TYPE: protein ( v i ) ORIGINAL SOURCE:
( A ) ORGANISM: Mycoplasma arthritidis
( B ) STRAIN: PG6
( G ) CELL TYPE: unicellular organism ( x i ) SEQUENCE DESCRIPTION: SEQ ID NO:4:

```
Met Lys Leu Arg Val Glu Asn Pro Lys Lys Ala Gln Lys His Phe Val
 1               5                  10                  15

Gln Asn Leu Asn Asn Val Val Phe Thr Asn Lys Glu Leu Glu Asp Ile
            20                  25                  30

Tyr Asn Leu Ser Asn Lys Glu Glu Thr Lys Glu Val Leu Lys Leu Phe
        35                  40                  45

Lys Leu Lys Val Asn Gln Phe Tyr Arg His Ala Phe Gly Ile Val Asn
    50                  55                  60

Asp Tyr Asn Gly Leu Leu Glu Tyr Lys Glu Ile Phe Asn Met Met Phe
65                  70                  75                  80

Leu Lys Leu Ser Val Val Phe Asp Thr Gln Arg Lys Glu Ala Asn Asn
                85                  90                  95

Val Glu Gln Ile Lys Arg Asn Ile Ala Ile Leu Asp Glu Ile Met Ala
            100                 105                 110

Lys Ala Asp Asn Asp Leu Ser Tyr Phe Ile Ser Gln Asn Lys Asn Phe
        115                 120                 125

Gln Glu Leu Trp Asp Lys Ala Val Lys Leu Thr Lys Glu Met Lys Ile
    130                 135                 140

Lys Leu Lys Gly Gln Lys Leu Asp Leu Arg Asp Gly Glu Val Ala Ile
145                 150                 155                 160

Asn Lys Val Arg Glu Leu Phe Gly Ser Asp Lys Asn Val Lys Glu Leu
                165                 170                 175

Trp Trp Phe Arg Ser Leu Leu Val Lys Gly Val Tyr Leu Ile Lys Arg
            180                 185                 190
```

-continued

Tyr Tyr Glu Gly Asp Ile Glu Leu Lys Thr Thr Ser Asp Phe Ala Lys
195 200 205

Ala Val Phe Glu Asp
210

( 2 ) INFORMATION FOR SEQ ID NO:5:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( v ) FRAGMENT TYPE: N-terminal fragment ( v i ) ORIGINAL SOURCE:
( A ) ORGANISM: Mycoplasma arthritidis
( B ) STRAIN: PG6
( G ) CELL TYPE: unicellular organism ( i x ) FEATURE:
( A ) NAME/KEY: N-terminus of mature MAM, with a Cys residue added at the N-end
( B ) LOCATION: Cys at N-terminal followed by MAM residues 1- 13
( D ) OTHER INFORMATION: does not inhibit cell proliferation ( x i ) SEQUENCE DESCRIPTION: SEQ ID NO:5:

Cys Met Lys Leu Arg Val Glu Asn Pro Lys Lys Ala Gln Lys
1 5 10

( 2 ) INFORMATION FOR SEQ ID NO:6:

( i ) SEQUENCE CHARACTERISTICS:
( A ) LENGTH: 19 amino acids
( B ) TYPE: amino acid
( D ) TOPOLOGY: linear ( i i ) MOLECULE TYPE: peptide ( v ) FRAGMENT TYPE: internal fragment plus C-terminal Cys ( v i ) ORIGINAL SOURCE:
( A ) ORGANISM: Mycoplasma arthritidis
( B ) STRAIN: PG6
( G ) CELL TYPE: unicellular organism ( i x ) FEATURE:
( B ) LOCATION: MAM residues 27-44, plus C-terminal Cys
( D ) OTHER INFORMATION: does not inhibit cell proliferation ( x i ) SEQUENCE DESCRIPTION: SEQ ID NO:6:

Lys Glu Leu Glu Asp Ile Tyr Asn Leu Ser Asn Lys Glu Glu Thr Lys
1 5 10 15

Glu Val Cys ( 2 ) INFORMATION FOR SEQ ID NO:7:

( i ) SEQUENCE CHARACTERISTICS:
( A ) LENGTH: 19 amino acids
( B ) TYPE: amino acid
( D ) TOPOLOGY: linear ( i i ) MOLECULE TYPE: peptide ( v ) FRAGMENT TYPE: internal fragment plus C-terminal Cys ( v i ) ORIGINAL SOURCE:
( A ) ORGANISM: Mycoplasma arthritidis -continued ( B ) STRAIN: PG6
( G ) CELL TYPE: unicellular organism ( i x ) FEATURE:
( A ) NAME/KEY: competitively inhibits MAM-induced cell proliferation
( B ) LOCATION: MAM residues 15 to 32, plus C-terminal Cys
( C ) IDENTIFICATION METHOD: in vitro competitive inhibition assay ( x i ) SEQUENCE DESCRIPTION: SEQ ID NO:7:

Phe Val Gln Asn Leu Asn Asn Val Val Phe Thr Asn Lys Glu Leu Glu
1 5 10 15

Asp Ile Cys ( 2 ) INFORMATION FOR SEQ ID NO:8:

( i ) SEQUENCE CHARACTERISTICS:
( A ) LENGTH: 27 amino acids
( B ) TYPE: amino acid
( D ) TOPOLOGY: linear ( i i ) MOLECULE TYPE: peptide ( v ) FRAGMENT TYPE: internal fragment ( v i ) ORIGINAL SOURCE:
( A ) ORGANISM: Mycoplasma arthritidis
( B ) STRAIN: PG6
( G ) CELL TYPE: unicellular organism ( i x ) FEATURE:
( B ) LOCATION: MAM residues 12 to 38

( x i ) SEQUENCE DESCRIPTION: SEQ ID NO:8:

Gln Lys His Phe Val Gln Asn Leu Asn Asn Val Val Phe Thr Asn Lys
1 5 10 15

Glu Leu Glu Asp Ile Tyr Asn Leu Ser Asn Lys
20 25

( 2 ) INFORMATION FOR SEQ ID NO:9:

( i ) SEQUENCE CHARACTERISTICS:
( A ) LENGTH: 27 amino acids
( B ) TYPE: amino acid
( D ) TOPOLOGY: linear ( i i ) MOLECULE TYPE: peptide ( v ) FRAGMENT TYPE: internal fragment ( v i ) ORIGINAL SOURCE:
( A ) ORGANISM: Staphylococcus aureus
( B ) STRAIN: S6
( G ) CELL TYPE: unicellular organism ( i x ) FEATURE:
( A ) NAME/KEY: staphylococcal enterotoxin B amino acid sequence having sequence similarity to MAM.
( B ) LOCATION: residues 39 to 65
( C ) IDENTIFICATION METHOD: computer searching for sequence similarities.

( x ) PUBLICATION INFORMATION:
( A ) AUTHORS: Jones, C.L.
Khan, S.A.
( B ) TITLE: Nucleotide Sequence of the Enterotoxin B Gene from Staphylococcus aureus
( C ) JOURNAL: J. Bacteriol.
( D ) VOLUME: 166
( E ) ISSUE: 1
( F ) PAGES: 29-33

-continued (G) DATE: APR-1986

(xi) SEQUENCE DESCRIPTION: SEQ ID NO:9:

Lys Ser Ile Asp Gln Phe Leu Tyr Phe Asp Leu Ile Tyr Ser Ile Lys
1 5 10 15

Asp Thr Lys Leu Gly Asn Tyr Asp Asn Val Arg
20 25

(2) INFORMATION FOR SEQ ID NO:10:

(i) SEQUENCE CHARACTERISTICS:
(A) LENGTH: 27 amino acids
(B) TYPE: amino acid
(D) TOPOLOGY: linear (ii) MOLECULE TYPE: peptide (v) FRAGMENT TYPE: internal fragment (vi) ORIGINAL SOURCE:
(A) ORGANISM: Staphylococcus aureus
(B) STRAIN: S6
(G) CELL TYPE: unicellular organism (ix) FEATURE:
(A) NAME/KEY: staphylococcal enterotoxin B amino acid sequence having sequence similarity to MAM.
(B) LOCATION: residues 56 to 82
(C) IDENTIFICATION METHOD: computer searching for sequence similarities.

(x) PUBLICATION INFORMATION:
(A) AUTHORS: Jones, C.L.
Khan, S.A.
(B) TITLE: Nucleotide Sequence of the Enterotoxin B Gene from Staphylococcus aureus
(C) JOURNAL: J. Bacteriol.
(D) VOLUME: 166
(E) ISSUE: 1
(F) PAGES: 29-33
(G) DATE: APR-1986

(xi) SEQUENCE DESCRIPTION: SEQ ID NO:10:

Thr Lys Leu Gly Asn Tyr Asp Asn Val Arg Val Glu Phe Lys Asn Lys
1 5 10 15

Asp Leu Ala Asp Lys Tyr Lys Asp Lys Tyr Val
20 25

(2) INFORMATION FOR SEQ ID NO:11:

(i) SEQUENCE CHARACTERISTICS:
(A) LENGTH: 27 amino acids
(B) TYPE: amino acid
(D) TOPOLOGY: linear (ii) MOLECULE TYPE: peptide (v) FRAGMENT TYPE: internal fragment (vi) ORIGINAL SOURCE:
(A) ORGANISM: Staphylococcus aureus
(G) CELL TYPE: unicellular organism (ix) FEATURE:
(A) NAME/KEY: staphylococcal enterotoxin C1 amino acid sequence having sequence similarity to MAM.
(B) LOCATION: residues 30 to 56
(C) IDENTIFICATION METHOD: computer searching for sequence similarities.

(x) PUBLICATION INFORMATION:
(A) AUTHORS: Bohach, G.A.

Schlievert, P.M.
( B ) TITLE: Nucleotide sequence of the staphylococcal enterotoxin C1 gene and relatedness to other pyrogenic exotoxins
( C ) JOURNAL: Mol. Gen. Genet.
( D ) VOLUME: 209
( F ) PAGES: 15-20
( G ) DATE: 1987

( x i ) SEQUENCE DESCRIPTION: SEQ ID NO:11:

Asp His Tyr Val Ser Ala Thr Lys Val Lys Ser Val Asp Lys Phe Leu
1 5 10 15

Ala His Asp Leu Ile Tyr Asn Ile Ser Asp Lys
20 25

( 2 ) INFORMATION FOR SEQ ID NO:12:

( i ) SEQUENCE CHARACTERISTICS:
( A ) LENGTH: 27 amino acids
( B ) TYPE: amino acid
( D ) TOPOLOGY: linear ( i i ) MOLECULE TYPE: peptide ( v ) FRAGMENT TYPE: internal fragment ( v i ) ORIGINAL SOURCE:
( A ) ORGANISM: Staphylococcus aureus
( G ) CELL TYPE: unicellular organism ( i x ) FEATURE:
( A ) NAME/KEY: staphylococcal enterotoxin C1 amino acid sequence having sequence similarity to MAM.
( B ) LOCATION: residues 121 to 147
( C ) IDENTIFICATION METHOD: computer searching for sequence similarities.

( x ) PUBLICATION INFORMATION:
( A ) AUTHORS: Bohach, G.A.
Schlievert, P.M.
( B ) TITLE: Nucleotide sequence of the staphylococcal enterotoxin C1 gene and relatedness to other pyrogenic toxins
( C ) JOURNAL: Mol. Gen. Genet.
( D ) VOLUME: 209
( F ) PAGES: 15-20
( G ) DATE: 1987

( x i ) SEQUENCE DESCRIPTION: SEQ ID NO:12:

Asn His Phe Asp Asn Gly Asn Leu Gln Asn Val Leu Ile Arg Val Tyr
1 5 10 15

Glu Asn Lys Arg Asn Thr Ile Ser Phe Glu Val
20 25

( 2 ) INFORMATION FOR SEQ ID NO:13:

( i ) SEQUENCE CHARACTERISTICS:
( A ) LENGTH: 27 amino acids
( B ) TYPE: amino acid
( D ) TOPOLOGY: linear ( i i ) MOLECULE TYPE: peptide ( v ) FRAGMENT TYPE: internal fragment ( v i ) ORIGINAL SOURCE:
( A ) ORGANISM: Staphylococcus aureus
( G ) CELL TYPE: unicellular organism ( i x ) FEATURE:
( A ) NAME/KEY: staphylococcal enterotoxin C1 amino acid sequence having sequence similarity to MAM.

( B ) LOCATION: residues 124 to 150
( C ) IDENTIFICATION METHOD: computer searching for sequence similarities.

( x ) PUBLICATION INFORMATION:
( A ) AUTHORS: Bohach, G.A.
Schlievert, P.M.
( B ) TITLE: Nucleotide sequence of the staphylococcal enterotoxin C1 gene and relatedness to other pyrogenic exotoxins
( C ) JOURNAL: Mol. Gen. Genet.
( D ) VOLUME: 209
( F ) PAGES: 15-20
( G ) DATE: 1987

( x i ) SEQUENCE DESCRIPTION: SEQ ID NO:13:

```
Asp Asn Gly Asn Leu Gln Asn Val Leu Ile Arg Val Tyr Glu Asn Lys
 1               5                   10                  15

Arg Asn Thr Ile Ser Phe Glu Val Gln Thr Asp
            20                   25
```

( 2 ) INFORMATION FOR SEQ ID NO:14:

( i ) SEQUENCE CHARACTERISTICS:
( A ) LENGTH: 27 amino acids
( B ) TYPE: amino acid
( D ) TOPOLOGY: linear ( i i ) MOLECULE TYPE: peptide ( v ) FRAGMENT TYPE: internal fragment ( v i ) ORIGINAL SOURCE:
( A ) ORGANISM: Streptococcus pyogenes
( G ) CELL TYPE: unicellular organism ( i x ) FEATURE:
( A ) NAME/KEY: streptococcal pyrogenic exotoxin C amino acid sequence having sequence similarity to MAM.
( B ) LOCATION: residues 109 to 135
( C ) IDENTIFICATION METHOD: computer searching for sequence similarities.

( x ) PUBLICATION INFORMATION:
( A ) AUTHORS: Goshorn, S.C.
Schlievert, P.M.
( B ) TITLE: Nucleotide Sequence of Streptococcal Pyrogenic Exotoxin Type C
( C ) JOURNAL: Infect. Immun.
( D ) VOLUME: 56
( E ) ISSUE: 9
( F ) PAGES: 2518-2520
( G ) DATE: SEP-1988

( x i ) SEQUENCE DESCRIPTION: SEQ ID NO:14:

```
Ser Gly Glu Ser Gln Gln Asn Leu Asn Asn Lys Ile Ile Leu Glu Lys
 1               5                   10                  15

Asp Ile Val Thr Phe Gln Glu Ile Asp Phe Lys
            20                   25
```

( 2 ) INFORMATION FOR SEQ ID NO:15:

( i ) SEQUENCE CHARACTERISTICS:
( A ) LENGTH: 17 amino acids
( B ) TYPE: amino acid
( D ) TOPOLOGY: linear ( i i ) MOLECULE TYPE: peptide ( v ) FRAGMENT TYPE: internal fragment ( v i ) ORIGINAL SOURCE:
( A ) ORGANISM: Mycoplasma arthritidis -continued ( B ) STRAIN: PG6
( G ) CELL TYPE: unicellular organism ( i x ) FEATURE:
( B ) LOCATION: MAM residues 16 to 32

( x i ) SEQUENCE DESCRIPTION: SEQ ID NO:15:

Val Gln Asn Leu Asn Asn Val Val Phe Thr Asn Lys Glu Leu Glu Asp
1 5 10 15

Ile ( 2 ) INFORMATION FOR SEQ ID NO:16:

( i ) SEQUENCE CHARACTERISTICS:
( A ) LENGTH: 26 amino acids
( B ) TYPE: amino acid
( D ) TOPOLOGY: linear ( i i ) MOLECULE TYPE: peptide ( v ) FRAGMENT TYPE: internal fragment ( v i ) ORIGINAL SOURCE:
( A ) ORGANISM: Mycoplasma arthritidis
( B ) STRAIN: PG6
( G ) CELL TYPE: unicellular organism ( i x ) FEATURE:
( B ) LOCATION: MAM residues 10 to 35

( x i ) SEQUENCE DESCRIPTION: SEQ ID NO:16:

Lys Ala Gln Lys His Phe Val Gln Asn Leu Asn Asn Val Val Phe Thr
1 5 10 15

Asn Lys Glu Leu Glu Asp Ile Tyr Asn Leu
20 25

( 2 ) INFORMATION FOR SEQ ID NO:17:

( i ) SEQUENCE CHARACTERISTICS:
( A ) LENGTH: 28 amino acids
( B ) TYPE: amino acid
( D ) TOPOLOGY: linear ( i i ) MOLECULE TYPE: peptide ( v ) FRAGMENT TYPE: internal fragment ( v i ) ORIGINAL SOURCE:
( A ) ORGANISM: Murine tumor virus 7

( i x ) FEATURE:
( B ) LOCATION: MTV7 residues 77 to 104

( x ) PUBLICATION INFORMATION:
( A ) AUTHORS: Beutner, U.
Frankel, W.N.
Cote, M.S.
Coffin, J.M.
Huber, B.T.
( B ) TITLE: Mls-1 is encoded by the long terminal repeat open reading frame of the mouse mammary tumor provirus Mtv-7
( C ) JOURNAL: Proc. Nat'l Acad. Sci. USA
( D ) VOLUME: 89
( F ) PAGES: 5432-5436
( G ) DATE: JUN-1992

( x i ) SEQUENCE DESCRIPTION: SEQ ID NO:17:

Ser Phe Asn Ser Ser Ser Val Gln Asp Tyr Asn Leu Asn Asn Ser Glu
1 5 10 15

Asn Ser Thr Phe Leu Leu Gly Gln Gly Pro Gln Pro
20 25

( 2 ) INFORMATION FOR SEQ ID NO:18:

( i ) SEQUENCE CHARACTERISTICS:
( A ) LENGTH: 26 amino acids
( B ) TYPE: amino acid
( D ) TOPOLOGY: linear ( i i ) MOLECULE TYPE: peptide ( v ) FRAGMENT TYPE: internal fragment ( v i ) ORIGINAL SOURCE:
( A ) ORGANISM: Murine tumor virus 7

( i x ) FEATURE:
( B ) LOCATION: MTV7 residues 115 to 140

( x ) PUBLICATION INFORMATION:
( A ) AUTHORS: Beutner, U.
Frankel, W.N.
Cote, M.S.
Coffin, J.M.
Huber, B.T.
( B ) TITLE: Mls-1 is encoded by the long terminal repeat open reading frame of the mouse mammary tumor provirus Mtv-7
( C ) JOURNAL: Proc. Nat'l Acad. Sci. USA
( D ) VOLUME: 89
( F ) PAGES: 5432-5436
( G ) DATE: JUN-1992

( x i ) SEQUENCE DESCRIPTION: SEQ ID NO:18:

```
Pro Ser Glu Ile Glu Ile Arg Met Leu Ala Lys Asn Tyr Ile Phe Thr
 1               5                  10                  15

Asn Lys Thr Asn Pro Ile Gly Arg Leu Leu
            20                  25
```

( 2 ) INFORMATION FOR SEQ ID NO:19:

( i ) SEQUENCE CHARACTERISTICS:
( A ) LENGTH: 26 amino acids
( B ) TYPE: amino acid
( D ) TOPOLOGY: linear ( i i ) MOLECULE TYPE: peptide ( v ) FRAGMENT TYPE: internal fragment ( v i ) ORIGINAL SOURCE:
( A ) ORGANISM: human immunodeficiency virus-1
( B ) STRAIN: 1R ( i x ) FEATURE:
( A ) NAME/KEY: GAG protein
( B ) LOCATION: residues 22 to 47

( x ) PUBLICATION INFORMATION:
( A ) AUTHORS: Starcich, B.R.
Hahn, B.H.
Shaw, G.M.
McNeely, P.D.
Modrow, S.
Wolf, H.
Parks, E.S.
Parks, W.P.
Josephs, S.F.
Gallo, R.C.
Wong-Staal, F.
( B ) TITLE: Identification and characterization of conserved and variable regions in the envelope gene of HTLV-III/LAV, the retrovirus of AIDS.
( C ) JOURNAL: Cell
( D ) VOLUME: 45
( F ) PAGES: 637-648

(G) DATE: 1986

(xi) SEQUENCE DESCRIPTION: SEQ ID NO:19:

Arg Pro Arg Gly Lys Lys Arg Tyr Lys Leu Lys His Ile Val Trp Ala
1 5 10 15

Ser Arg Glu Leu Glu Arg Phe Ala Val Asn
20 25

(2) INFORMATION FOR SEQ ID NO:20:

(i) SEQUENCE CHARACTERISTICS:
(A) LENGTH: 26 amino acids
(B) TYPE: amino acid
(D) TOPOLOGY: linear (ii) MOLECULE TYPE: peptide (v) FRAGMENT TYPE: internal fragment (vi) ORIGINAL SOURCE:
(A) ORGANISM: human immunodeficiency virus-1
(B) STRAIN: 1R (ix) FEATURE:
(A) NAME/KEY: GAG protein
(B) LOCATION: residues 129 to 154

(x) PUBLICATION INFORMATION:
(A) AUTHORS: Starcich, B.R.
Hahn, B.H.
Shaw, G.M.
McNeely, P.D.
Modrow, S.
Wolf, H.
Parks, E.S.
Parks, W.P.
Josephs, S.F.
Gallo, R.C.
Wong-Staal, F.
(B) TITLE: Identification and characterization of conserved and variable regions in the envelope gene of HTLV-III/LAV, the retrovirus of AIDS.
(C) JOURNAL: Cell
(D) VOLUME: 45
(F) PAGES: 637-648
(G) DATE: 1986

(xi) SEQUENCE DESCRIPTION: SEQ ID NO:20:

Ser Gln Asn Tyr Pro Ile Val Gln Asn Leu Gln Gly Gln Met Val His
1 5 10 15

Gln Ala Ile Ser Pro Arg Thr Leu Asn Ala
20 25

(2) INFORMATION FOR SEQ ID NO:21:

(i) SEQUENCE CHARACTERISTICS:
(A) LENGTH: 26 amino acids
(B) TYPE: amino acid
(D) TOPOLOGY: linear (ii) MOLECULE TYPE: peptide (v) FRAGMENT TYPE: internal fragment (vi) ORIGINAL SOURCE:
(A) ORGANISM: human immunodeficiency virus-1
(B) STRAIN: Z321

(ix) FEATURE:
(A) NAME/KEY: envelope protein
(B) LOCATION: residues 543 to 568

(x) PUBLICATION INFORMATION:

-continued ( A ) AUTHORS: Srinivasan, A.
York, D.
Butler, D., Jr.
Jannoun- Nasr, R.
Getchell, J.
McCormick, J.
Ou, C.- Y.
Myers, G.
Smith, T.
Chen, E.
Flaggs, G.
Berman, P.
Schochetman, G.
Kalyanaramen, S.
( B ) TITLE: Molecular characterization of HIV-1 isolated from a serum collected in 1976: nucleotide sequence comparison to recent isolates and generation of hybrid HIV.
( C ) JOURNAL: AIDS Res. Hum. Retroviruses
( D ) VOLUME: 5
( F ) PAGES: 121-129
( G ) DATE: 1989

( x i ) SEQUENCE DESCRIPTION: SEQ ID NO:21:

Arg Leu Leu Ser Gly Ile Val Gln Gln Gln Asn Asn Leu Leu Arg Ala
1 5 10 15

Ile Glu Ala Gln Gln His Leu Leu Lys Leu
20 25

( 2 ) INFORMATION FOR SEQ ID NO:22:

( i ) SEQUENCE CHARACTERISTICS:
( A ) LENGTH: 26 amino acids
( B ) TYPE: amino acid
( D ) TOPOLOGY: linear ( i i ) MOLECULE TYPE: peptide ( v ) FRAGMENT TYPE: internal fragment ( v i ) ORIGINAL SOURCE:
( A ) ORGANISM: human immunodeficiency virus-1
( B ) STRAIN: Z321

( i x ) FEATURE:
( A ) NAME/KEY: envelope protein
( B ) LOCATION: residues 600 to 625

( x ) PUBLICATION INFORMATION:
( A ) AUTHORS: Srinivasan, A.
York, D.
Butler, D., Jr.
Jannoun- Nasr, R.
Getchell, J.
McCormick, J.
Ou, C.- Y.
Myers, G.
Smith, T.
Chen, E.
Flaggs, G.
Berman, P.
Schochetman, G.
Kalyanaramen, S.
( B ) TITLE: Molecular characterization of HIV-1 isolated from a serum collected in 1976: nucleotide sequence comparison to recent isolates and generation of hybrid HIV.
( C ) JOURNAL: AIDS Res. Hum. Retroviruses
( D ) VOLUME: 5
( F ) PAGES: 121-129
( G ) DATE: 1989

( x i ) SEQUENCE DESCRIPTION: SEQ ID NO:22:

Gly Lys Ile Ile Cys Pro Thr Asn Val Pro Trp Asn Ser Ser Trp Ser
1 5 10 15

Asn Lys Ser Gln Ser Asp Ile Trp Asp Lys
20 25

( 2 ) INFORMATION FOR SEQ ID NO:23:

( i ) SEQUENCE CHARACTERISTICS:
( A ) LENGTH: 26 amino acids
( B ) TYPE: amino acid
( D ) TOPOLOGY: linear ( i i ) MOLECULE TYPE: peptide ( v ) FRAGMENT TYPE: internal fragment ( v i ) ORIGINAL SOURCE:
( A ) ORGANISM: human immunodeficiency virus-1
( B ) STRAIN: Z321

( i x ) FEATURE:
( A ) NAME/KEY: envelope protein
( B ) LOCATION: residues 629 to 654

( x ) PUBLICATION INFORMATION:
( A ) AUTHORS: Srinivasan, A.
York, D.
Butler, D., Jr.
Jannoun- Nasr, R.
Getchell, J.
McCormick, J.
Ou, C.- Y.
Myers, G.
Smith, T.
Chen, E.
Flaggs, G.
Berman, P.
Schochetman, G.
Kalyanaramen, S.
( B ) TITLE: Molecular characterization of HIV-1 isolated from a serum collected in 1976: nucleotide sequence comparison to recent isolates and generation of hybrid HIV.
( C ) JOURNAL: AIDS Res. Hum. Retroviruses
( D ) VOLUME: 5
( F ) PAGES: 121-129
( G ) DATE: 1989

( x i ) SEQUENCE DESCRIPTION: SEQ ID NO:23:

Leu Glu Trp Asp Lys Glu Val Ser Asn Tyr Thr Gln Val Ile Tyr Asn
1 5 10 15

Leu Ile Glu Glu Ser Gln Thr Gln Gln Glu
20 25

( 2 ) INFORMATION FOR SEQ ID NO:24:

( i ) SEQUENCE CHARACTERISTICS:
( A ) LENGTH: 8 amino acids
( B ) TYPE: amino acid
( D ) TOPOLOGY: linear ( i i ) MOLECULE TYPE: protein ( v ) FRAGMENT TYPE: internal fragment ( v i ) ORIGINAL SOURCE:
( A ) ORGANISM: Human Immunodeficiency Virus ( i x ) FEATURE:
( A ) NAME/KEY: internal region of GAG protein
( B ) LOCATION: 135 to 142
( D ) OTHER INFORMATION: contains conservative sequence homology with MAM amino acids 16-23

( x i ) SEQUENCE DESCRIPTION: SEQ ID NO:24:

Val Gln Asn Leu Gln Gly Gln Met
1 5

-continued ( 2 ) INFORMATION FOR SEQ ID NO:25:

( i ) SEQUENCE CHARACTERISTICS:
( A ) LENGTH: 8 amino acids
( B ) TYPE: amino acid
( D ) TOPOLOGY: linear ( i i ) MOLECULE TYPE: protein ( v ) FRAGMENT TYPE: internal fragment ( v i ) ORIGINAL SOURCE:
( A ) ORGANISM: Human Immunodeficiency Virus
( B ) STRAIN: Z321

( i x ) FEATURE:
( A ) NAME/KEY: internal region of envelope protein
( B ) LOCATION: 549 to 556
( D ) OTHER INFORMATION: contains conservative sequence homology with MAM amino acids 16-23

( x i ) SEQUENCE DESCRIPTION: SEQ ID NO:25:

```
Val Gln Gln Gln Asn Asn Leu Leu
 1               5
```

( 2 ) INFORMATION FOR SEQ ID NO:26:

( i ) SEQUENCE CHARACTERISTICS:
( A ) LENGTH: 8 amino acids
( B ) TYPE: amino acid
( D ) TOPOLOGY: linear ( i i ) MOLECULE TYPE: protein ( v ) FRAGMENT TYPE: internal fragment ( v i ) ORIGINAL SOURCE:
( A ) ORGANISM: Murine Tumor Virus 7

( i x ) FEATURE:
( B ) LOCATION: 83 to 90
( D ) OTHER INFORMATION: contains conservative sequence homology with MAM amino acids 16-23

( x i ) SEQUENCE DESCRIPTION: SEQ ID NO:26:

```
Val Gln Asp Tyr Asn Leu Asn Asn
 1               5
```

MYCOPLASMA ARTHRITIDIS T-CELL MITOGEN

This invention was made with government support under grants AI12103 and AM02255 awarded by the U.S. Department of Health and Human Services. The government has certain rights in the invention.

BACKGROUND OF THE INVENTION

This invention relates to compositions and methods for preventing human diseases including autoimmune diseases. More particularly, this invention relates to nucleic acid sequences and amino acid sequences of *Mycoplasma arthritidis* mitogen (MAM), synthetic oligonucleotides and peptides having such sequences, a method of purifying MAM to electrophoretic and sequence homogeneity, and methods of using such sequences and purified MAM in preventing human disease.

In autoimmune disease, a breakdown of self-tolerance leads to generation of an immune response against a specific target antigen or antigens. Microbial agents have long been thought to trigger autoimmune diseases by possessing antigenic determinants that are crossreactive with antigens on target organs. More recently, it has been suggested that superantigens derived from bacteria, P. Marrack & J. Kappler, 248 *Science* 705 (1990); B. Fleischer, 10 *Immunol. Today* 262 (1989), mycoplasma, B. Cole & C. Atkin, 12 *Immunol. Today* 271 (1991), or viruses, W. Frankel et al., 349 *Nature* 526 (1991); P. Dyson et al., 349 *Nature* 531 (1991); Y. Choi et al., 350 *Nature* 203 (1991), may initiate autoimmune disease by activating specific anti-self T cell clones, J. White et al., 56 *Cell* 27 (1989); B. Cole et al., 144 *J. Immunol.* 425 (1990), X. Paliard et al., 253 *Science* 325 (1991), or by forming a superantigen bridge that crosslinks helper T ($T_H$) cells with pre-immune B cells, thereby causing polyclonal B cell activation and secretion of autoimmune antibodies, S. Friedman et al., 34 *Arthritis Rheum.* 468 (1991), W. Mourad et al., 170 *J. Exp. Med.* 2011 (1989). In fact, recent studies have shown that MAM can trigger, enhance, and exacerbate experimental autoimmune collagen-induced arthritis (CIA). B. Cole & M. Griffiths, 36 *Arthritis Rheum.* 994 (1993).

Superantigens are potent mitogens that activate T cells by a unique pathway that binds the major histocompatibility complex (MHC) molecules on accessory cell or B lymphocyte surfaces with specific β-chain variable regions ($V_\beta$) of the α/β T cell receptor for antigen (TCR) present on T cells. Thus, a particular superantigen may be recognized by virtually all T cells that utilize a single or small group of TCR $V_\beta$ gene families. While there is some overlap, each superantigen is recognized by its use of a distinct and characteristic set of TCR $V_\beta$ gene families. Further, superantigens bind selectively and with high affinity to class II MHC molecules. In the absence of antigen processing and in a non-MHC-restricted manner, superantigen-class II MHC antigen complexes on the antigen-presenting cell surface trigger the proliferation of T cells expressing the relevant TCR $V_\beta$ gene products. Finally, the in vivo presence of superantigens profoundly alters the T cell repertoire. During the process of negative selection within the thymus, a superantigen clonally eliminates thymocytes with TCR that bear $V_\beta$ gene products that recognize exactly that superantigen. Superantigens include several staphylococcal enterotoxins, streptococcal pyrogenic exotoxins, a fragment of the group A streptococcus M protein, murine self antigens such as the Mls loci gene products (now known to be encoded by murine tumor retroviruses) and an unknown B cell-specific antigen, and *Mycoplasma arthritidis* T cell mitogen (MAM).

Mycoplasmas are the smallest self-replicating prokaryotes and are parasites of humans, birds, insects, plants, and virtually all other higher life forms. Mycoplasmas are the most common cause of naturally-occurring acute and chronic arthritis in many animal species. *M. arthritidis* is a naturally-occurring arthritogen of rodents that causes a chronic, relapsing disease that, histologically, closely resembles human rheumatoid arthritis. MAM was discovered when live organisms and culture supernatants of *M. arthritidis* were shown to induce the proliferation of, and elicit the differentiation of, cytolytic cells in mouse splenocytes. B. Cole et al., 127 *J. Immunol.* 1931 (1981). An insoluble, presumably membrane-bound B-cell mitogen was found to be associated with mycoplasma cells and was stable at 100° C. In contrast, a soluble T-cell mitogen was present in culture supernatants and was heat labile at 56° C. This heat labile T-cell mitogen is MAM. MAM was then shown to be a potent T-cell mitogen and inducer of gamma-interferon (IFN-γ) for both murine and human lymphocytes. B. Cole et al., 128 *J. Immunol.* 2013 (1982); B. Cole & R. Thorpe, 131 *J. Immunol.* 2392 (1983); B. Cole & R. Thorpe, 43 *Infect. Immun.* 302 (1984); T. Moritz et al., 20 *Scand. J. Immunol.* 365 (1984); H. Kirchner et al., 20 *Scand. J. Immunol.* 133 (1984); H. Kirchner et al., 4 *J. Interferon Res.* 389 (1984).

MAM is produced to maximal titer in senescent broth cultures of *M. arthritidis*. Purification is difficult because MAM is produced in small amounts, is heat and acid (pH<7.0) labile, and has great affinity for surfaces and large molecules, especially nucleic acids. Gel filtration of culture supernatants, at an ionic strength of about 0.5M, indicated that MAM has a molecular mass of about 15 kD whereas PAGE suggested the molecule was about 30 kD. C. Atkin et al., 137 *J. Immunol.* 1581 (1986); H. Kirchner et al., 24 *Scand. J. Immunol.* 245 (1986). Although Kirchner et al. claimed partial purification of MAM, their purification steps would have yielded ≦200-fold purification in the best of hands. Since their mitogenic assay was merely qualitative, they were unable to show yield or specific activity (mitogenicity per unit protein). J. Homfeld et al., 7 *Autoimmunity* 317 (1990), have also described partial purification of MAM. Using a quantitative assay for MAM, C. Atkin et al., 137 *J. Immunol.* 1581 (1986), to achieve 200,000-fold purification. The calculated purification of MAM by the final gel filtration step implies measurement of protein, but the method was not given nor was a profile of protein or absorbance shown. Active fractions corresponded to the elution volumes of 15–20 kD standards, but no stainable protein by SDS-PAGE was identified nor was an amino acid sequence reported.

One of the major activities of MAM is its ability to cause a proliferation of lymphocytes from certain strains of mice, but not of others. Lymphocytes from BALB/c and C3H mice are readily activated whereas those of C57BL/10 mice fail to undergo proliferation in response to exposure to MAM. This negative or weak response of C57BL/10 mice enabled mapping one of the genes which control MAM reactivity to the I-E region of the murine H-2 MHC. Dependence upon MHC-bearing accessory cells for MAM-induced T-cell proliferation was consistent with this conclusion. This specificity for I-E bearing cells suggested that the I-E molecule might be the binding site for MAM. The fact that only splenocytes from I-E-bearing mouse strains could remove MAM activity from solution and liposomes with incorporated I-E, but not with I-A, molecules could present MAM to T cells supported this hypothesis. There is substantial evidence that the conserved α chain of the I-E molecule, or a combinatorial determinant between $E_\alpha$ and other β chains, bears the MAM receptor. Evidence of this includes ATFR5 mice which lack $E_\beta$ respond to MAM through combinatorial $E_\alpha A_\beta$ molecules, antibodies to a monoclonal antibody specific for $E_\alpha$ totally block MAM-induced proliferation, $E_\alpha$ transgenic mice on a C57BL/10 background present MAM, and transfected fibroblasts expressing $E_\alpha E_\beta$ or $E_\alpha A_\beta$ present MAM, whereas fibroblasts expressing $A_\alpha A_\beta$ do not. B. Cole et al., 127 *J. Immunol.* 1931 (1981); B. Cole et al., 128 *J. Immunol.* 2013 (1982); B. Cole et al., 129 *J. Immunol.* 1352 (1982); B. Cole et al., 136 *J. Immunol.* 3572 (1986); M. Bekoff et al., 139 *J. Immunol.* 3189 (1987); M. Matthes et al., 18 *Eur. J. Immunol.* 1733 (1988); B. Cole et al., 144 *J. Immunol.* 420 (1990) .

MAM, like other superantigens, is recognized by $V_\beta$ chain segments of the α/β TCR. This was demonstrated in progeny of test-crosses between RIIIS mice, which have massive deletions in their $V_\beta$ α/β T-cell repertoire, with (RIIIS× B10.RIII)F1 hybrids. B10.RIII mice contains all $V_\beta$ genes. Reactivity of lymphocytes with MAM cosegregated with expression of $V_\beta$8-bearing cells. Thus, at least the $V_\beta$8 TCR gene family was involved in recognition of MAM. In other experiments, clonal expansion of MAM-reactive BALB/c cells in vitro showed the activated cells expressed $V_\beta$8.1, $V_\beta$8.2, $V_\beta$8.3, and $V_\beta$6. MAM expansion of C57BR lymphocytes, which lack the $V_\beta$8 genes, resulted in strong expression of $V_\beta$6 in the activated population. Similarly, it has been shown that MAM can use TCRs expressing $V_\beta$5.1. These specificities of MAM for certain TCR genes was reported in B. Cole et al., 144 *J. Immunol.* 425 (1990); L. Baccala et al., 35 *Arthritis Rheum.* 434 (1992). In rats, MAM-reactive $V_\beta$ are homologous to the MAM-reactive $V_\beta$ of mice, with one exception. Engagement of rat $V_\beta$5.1, $V_\beta$6, $V_\beta$8.1, and $V_\beta$8.2, but not $V_\beta$8.3 were observed. In humans, the engaged $V_\beta$ included primarily $V_\beta$19.1 (alternatively termed $V_\beta$17.1) and, to a lesser extent, $V_\beta$3.1, $V_\beta$11.1, $V_\beta$12.1, and $V_\beta$13.1. R. Baccala et al., 35 *Arthritis Rheum.* 434 (1992). More recent experiments have shown that both genomic composition and allelic polymorphisms at the $V_\beta$ chain segment of the TCR exert profound effects upon the pattern of $V_\beta$ that are used by MAM. Thus in $V_\beta^b$ haplotype mice without genomic deletions of $V_\beta$ genes, $V_\beta$5.1, 6, 8.1, 8.2, and 8.3 engage MAM. In $V_\beta^a$ mice, with deletions in $V_\beta$5.1 to 5.3, 8.1 to 8.3, 9, 11, 12, and 13, there was significant expansion of $V_\beta$6-expressing cells and lesser expansions of $V_\beta$1-, 7-, and 16-expressing cells. In $V_\beta^a$ mice, with deletions of the same $V_\beta$ genes deleted in $V_\beta^a$ and additional deletions in $V_\beta$6, 15, and 17, there was a dominant expansion of $V_\beta$7 and $V_\beta$1, and a slight expansion of $V_\beta$3.1-expressing cells. B. Cole et al., 150 *J. Immunol.* 3291 (1993). Usage of $V_\beta$8 gene products is fairly common among other microbial superantigens, however $V_\beta$6 is only used by MAM and the Mls $1^a$ antigen now known to be a murine retroviral superantigen.

MAM can also activate human peripheral blood lymphocytes; this reaction too is dependent upon MHC molecules. The human MHC HLA-DR molecule, the equivalent of the murine H2 I-E molecule, appears to possess the MAM binding site. Evidence of this includes inhibition of T-cell proliferation by anti-HLA-DR antibodies, production of IFN-γ and induction of cytolytic cells in response to MAM, and presentation of MAM to human T-cells by cells transfected with I-E and the inhibition of the response by anti-I-E monoclonal antibodies. MAM can produce proliferation of human T-cells regardless of whether the cells express CD4 or CD8 molecules. TCR α/β-negative, γ/δ-positive cells also respond to MAM in the presence of appropriate accessory cells. R. Daynes et al., 129 *J. Immunol.* 936 (1982); B. Cole & R. Thorpe, 131 *J. Immunol.* 2392 (1983); M. Matthes et al., 18 *Eur. J. Immunol.* 1733 (1988); R. Baccala et al., 35 *Arthritis Rheum.* 434 (1992).

The response of human cells to MAM has always been found to be weaker than that of mouse cells and weaker than to lectin mitogens. In a direct comparison, human cells responded better to staphylococcal superantigens than to MAM, and mouse cells responded better to MAM. B. Fleischer et al., 146 *J. Immunol.* 11 (1991). This difference seems to issue from differences in the MHC/superantigen interaction since lymphocytes from transgenic mice expressing human MHC molecules respond better to staphylococcal superantigens than to MAM.

The apparent ability of individual superantigen molecules to interact simultaneously with MHC molecules on accessory cells and B cells, as well as with $V_\beta$ TCRs on T-cells, raises the possibility that superantigens might be able to initiate a B-$T_H$ cell collaboration resulting in polyclonal B cell activation. Peripheral blood lymphocytes from normal individuals or rheumatoid arthritis patients secreted significantly higher levels of IgG when co-cultured in vitro with MAM and pokeweed mitogen. Further, purified B cell cultures or B cells incubated with MAM-reactive $T_H$ cells failed to secrete significant levels of IgM. However, when B cells were briefly exposed to MAM or when MAM was added to B-$T_H$ cell mixtures, high levels of IgM were produced. This is important because abnormal B-$T_H$ cell interactions mimic the interaction seen in graft versus host disease that has been used as a model of systemic lupus erythematosus (SLE). In SLE, abnormal B cell reactivity results in production of a wide range of autoantibodies. P. Emery et al., 12 *J. Rheumatol.* 217 (1985); J. Tumang et al., 171 *J. Exp. Med.* 2153 (1990); S. Friedman et al., 34 *Arthritis Rheum.* 468 (1991).

*M. arthritidis* also causes a severe suppurative arthritis in rats which can also be associated with uveitis, C. Thirkill & D. Gregerson, 36 *Infect. Immun.* 775 (1982), conjunctivitis, urethritis, lethargy, and paralysis, J. Ward & R. Jones, 5 *Arthritis Rheum.* 163 (1962). MAM can activate rat lymphocytes. B. Cole et al., 36 *Infect. Immun.* 662 (1982). Splenic cells from inbred rat strains August, Buffalo, DA, Lewis, Wistar Furth, and (LEW×BN)F1 all responded well to MAM, but BN and MAXX rats responded very weakly or not at all. Genetic analysis showed that non-RT1 genes control responsiveness to MAM. Both responder and non-responder splenic cells could bind MAM. These results contrast with the results obtained with non-responder mouse strains, wherein the cells failed to bind MAM due to the absence of the $E_\alpha$ chain of the I-E molecule. B. Cole et al., 129 *J. Immunol.*1352 (1982); B. Cole et al., 136 *J. Immunol.* 2364 (1986).

Interestingly, the genetics of MAM-induced activation of rat lymphocytes resembles that of susceptibility to two experimentally-induced autoimmune diseases, experimental allergic encephalomyelitis (EAE) and collagen-induced arthritis (CIA). Thus, (LEW×BN)F1 rats are susceptible to both EAE and CIA, and responsiveness to MAM is a dominant trait, whereas (DA×BN)F1 rats are resistant to both EAE and CIA, and responsiveness to MAM is recessive. In both EAE and CIA, T-cells expressing $V_\beta$ TCRs are involved in disease pathogenesis. Since rat and mouse $V_\beta$ TCRs are quite similar, it is not surprising that MAM also activates rat $V_\beta$8-bearing T-cells. L. Baccala et al., 35 *Arthritis Rheum.* 434 (1992).

Importantly, this similarity between the genetic predisposition to CIA and lymphocyte reactivity to MAM is now known to be due to involvement of similar $V_\beta$ chain segments of the TCR on T cell surfaces. Thus, T cells bearing $V_\beta6$, $V_\beta7$. and $V_\beta8$ participate in CIA. T. Haqqi et al., 89 *Proc. Nat'l Acad. Sci USA* 1253 (1992). These same $V_\beta$ TCRs are also activated by MAM. B. Cole et al., 150 *J. Immunol.* 3291 (1993), thus presenting a mechanism whereby superantigens might activate autoimmune disease. In fact, recent studies, B. Cole & M. Griffiths, 36 *Arthritis Rheum.* 944 (1993), have demonstrated that the intravenous injection of MAM (1) into mice suboptimally immunized with collagen causes a triggering of arthritis, (2) into mice convalescing from CIA results in a flare of disease activity, and (3) into mice just after injection of collagen causes an acceleration of the development of arthritis.

MAM is also thought to play a role in the pathogenicity of *M. arthritidis* by causing immunosuppression of the host. *M. arthritidis* is frequently harbored in the respiratory tract of apparently healthy mice and rats. Its presence may be undetectable without extensive culturing since an antibody response may not be present. M. Davidson et al., 8 *Curr. Microb.* 205 (1983). Even in experimentally-injected mice and rats, where complement-fixing antibodies are rapidly produced, the immune response to *M. arthritidis* is defective. Neutralizing or growth-inhibiting antibodies, which play a major role in the control of mycoplasma infections, are not produced against *M. arthritidis* in rodents. Opsonizing antibodies are likewise not produced. Probably for these reasons, mycoplasmemia persists for up to 3 weeks in the peripheral circulation of intravenously-injected animals. B. Cole et al., 98 *J. Bacteriol.* 930 (1969); B. Cole & J. Ward, 7 *Infect. Immun.* 691 (1973); B. Cole & J. Ward, 8 *Infect. Immun.* 199 (1973).

MAM may be responsible for depressed host defenses. Mycoplasmas are cleared faster from the peripheral circulation of mouse strains which lack functional I-E molecules than from strains possessing I-E. B. Cole et al., 41 *Infect. Immun.* 1010 (1983). Lymphocytes taken from I-E-bearing mice injected intravenously with MAM exhibit an impaired ability to proliferate in response to MAM, and, to a lesser extent, to lectin mitogens. B. Cole & D. Wells, 58 *Infect. Immun.* 228 (1990). MAM also appears to suppress other T-cell functions, such as contact sensitivity to dinitrofluorobenzene (DNFB) and can prolong skin grafts across H-2 and non-H-2 barriers. In contrast, MAM appears not to have any consistent suppressive effect in vivo on B-cell functions, but, instead, enhances B-cell activity.

MAM also appears at least partially responsible for reactions involving toxicity and necrosis in experimentally-injected mice. One of the earliest symptoms following intravenous injection of large numbers of *M. arthritidis* is a toxic shock syndrome that is analogous to the human condition caused by a staphylococcal superantigen. Symptoms include lethargy, ruffled fur, conjunctivitis, fecal impaction, and death in some individuals. These effects were H-2 restricted in that animals with MAM-reactive lymphocytes were susceptible, whereas animals with MAM-nonreactive lymphocytes were resistant. In part, this reaction may be due to liberation of lymphokines and other inflammatory molecules mediated by MAM-induced activation of lymphocytes and macrophages since large doses of highly purified MAM yielded a similar toxic syndrome, but of much lesser duration and severity. B. Cole et al., 41 *Infect. Immun.* 1010 (1983); B. Cole & D. Wells, 58 *Infect. Immun.* 228 (1990).

MAM also appears to play a role in dermal necrosis induced by subcutaneous injection of *M. arthritidis* in susceptible animals. Susceptible mice possess functional I-E, whereas mice lacking functional I-E developed a suppurative abscess but without dermal damage. B. Cole et al., 85 *J. Invest. Dermatol.* 357 (1985).

OBJECTS AND SUMMARY OF THE INVENTION

An object of the present invention is to provide MAM that is purified to homogeneity.

Another object of the invention is to provide a method of purifying MAM to homogeneity.

A further object of the invention is to provide a purified oligonucleotide containing a nucleotide sequence encoding MAM.

Yet another object of the invention is to provide an array of oligopeptides that either mimic or inhibit various biological activities of MAM.

A further objective of the invention is to provide homogeneous MAM or specific MAM peptides for use as reagents to modify immune reactivity in vitro or in vivo and to establish model systems to study the mechanisms of development of autoimmune disease.

Still another object of the invention is to provide a method of blocking flares of human diseases that are caused by exposure to superantigens.

Another object of the invention is to provide a method of immunizing against human diseases that are caused, triggered by, or made more severe by exposure to superantigens.

These and other objects may be accomplished by providing a method of purifying MAM to electrophoretic and sequence homogeneity from senescent cultures of *M. arthritidis* by recovering culture components that are soluble in 50% saturated $(NH_4)_2SO_4$ and insoluble in 80% saturated $(NH_4)_2SO_4$. These culture components are then back extracted in 1M $(NH_4)_2SO_4$; insoluble residues are sedimented and discarded while soluble components are retained. These soluble components are subjected to fractionation by gel filtration in very high ionic strength, slightly alkaline buffer, and fractions containing proteins of approximate molecular weight of 30,000 are recovered. These fractions are pooled, then the buffer of the pooled fractions is changed to low conductivity neutral buffer. Pool components that are retained on a cation exchange column after a starting buffer wash are eluted as a single 280 nm-absorbing fraction by frontal elution with neutral high salt buffer. The buffer of this recovered fraction is again changed to low conductivity neutral buffer; the many protein components of the single fraction are then fractionated by linear gradient elution with a high salt buffer on an FPLC (the proprietary "Fast Protein Liquid Chromatography" system of Pharmacia-LKB Biotechnology, Inc., Piscataway, N.J.) cation exchange chromatographic column. Active fractions, as determined by murine lymphocyte proliferation assay, are placed in high molarity salt buffer and subjected to FPLC hydrophobic interaction chromatography with reverse gradient elution to low salt. Elution of proteins simultaneously monitored at 214 and 280 nm. The minuscule, last-eluting peak is recovered in one or two small fractions, and is homogeneous MAM. Another aspect of the invention is providing homogeneous MAM protein purified by the method summarized above. Only by having homogeneous MAM preparations can sequence information be obtained. Such sequence was determined for the N-terminal 54 amino acids of MAM by direct sequencing by the Edman method, yielding the amino acid sequence listed as SEQ ID NO:1.

Another aspect of the invention is providing a purified oligonucleotide having a nucleotide sequence encoding MAM. The MAM gene was selected from a phage library of clones that spanned the entire genome of *M. arthritidis* PG6. This was achieved by first designing an oligonucleotide probe, SEQ ID NO:2, from a reverse translation of SEQ ID NO:1. This probe was used to select clones containing parts or all of the MAM gene, which clones were ordered and sequenced to yield the complete nucleotide sequence of the MAM gene, SEQ ID NO:3. It was thus determined that the MAM gene encodes a 39 amino acid signal or pre-peptide and a 213 amino acid mature MAM, SEQ ID NO:4.

Another aspect of the invention is providing an oligopeptide that inhibits MAM-induced cell proliferation. Three synthetic peptides, SEQ ID NO:5, SEQ ID NO:6, and SEQ ID NO:7, corresponding to amino acids 1–13, 27–44, and 15–32 of mature MAM were made. In competitive inhibition assays in vitro, the peptide having the sequence disclosed in SEQ ID NO:7 inhibited MAM-induced cell proliferation while SEQ ID NO:5 and SEQ ID NO:6 did not.

Another aspect of the invention is providing therapeutic regimens for the treatment of human diseases that are caused, triggered, or exacerbated by exposure to superantigens. Superantigens have been postulated to play roles in the development of human rheumatic diseases as well as of AIDS. Treatments may include immunization of individuals against a superantigen or derivative peptide, or injection of homologous peptides to directly block action of the superantigen. Amino acid sequence comparisons of MAM to bacterial superantigens, murine tumor virus superantigens, HIV and other retrovirus superantigens, and certain regulatory proteins showed small regions of conservative sequence homology. These regions were not co-linear as regards N-to-C-terminal alignment of the proteins and thus could not represent evolutionarily divergent protein—protein homologies; these regions were on the contrary considered as "potential shared epitopes" that might arise by evolutionary convergence of fundamentally different proteins. One such "potential shared epitope" was within the sequence of the oligopeptide identified as SEQ ID NO:7 and which inhibited MAM-induced cell proliferation in vitro. Administering effective doses of oligopeptides containing conservative homologous regions will permit blocking of superantigen disease-causing activity or immunization against the superantigens to prevent human diseases caused by exposure to superantigens. Similarly, the ability to block or mimic the various biological activities of MAM in animals and tissue culture would be of tremendous experimental utility.

BRIEF DESCRIPTION OF THE DRAWINGS

FIG. 6 shows sequence similarities of Gram-positive bacterial superantigens to potential epitopic region 1 of MAM.

FIG. 7 shows sequence similarities of retroviral superantigens and HIV-1 proteins to potential epitopic region 1 of MAM.

DETAILED DESCRIPTION OF THE INVENTION

Purification to Homogeneity of MAM

Figure 1:
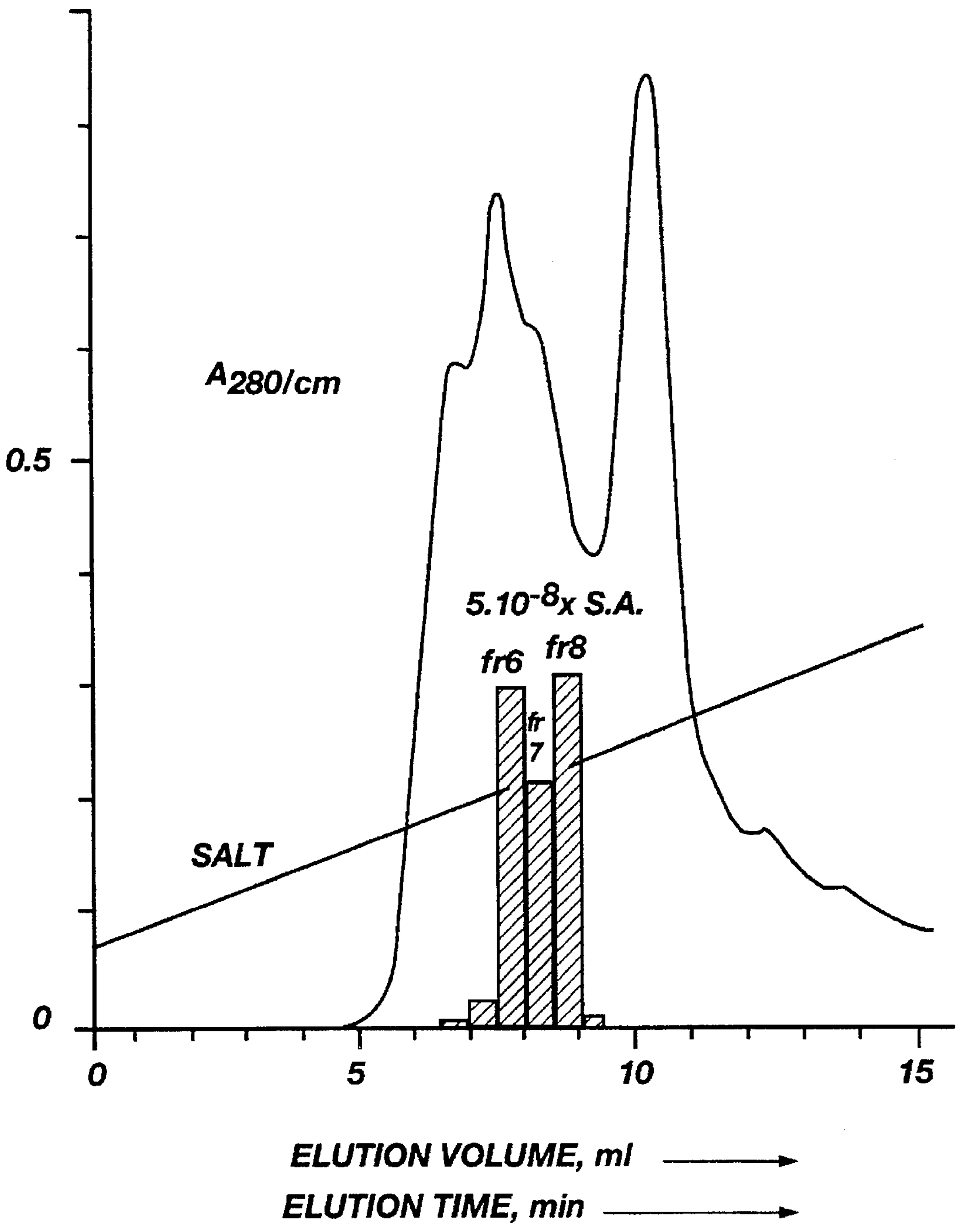
FIG. 1 shows an elution profile from the second cation exchange chromatography step of MAM purification on Mono-S Sepharose and the specific activity of the fractions.

Senescent cultures of various strains of *M. arthritidis*, such as 14124p10 and PG-6, contain MAM as a soluble, extracellular protein. MAM in typical cultures has great affinity for, and is thus difficult or impossible to separate from nucleic acids and other soluble macromolecules that are present in the classic Edward-Hayflick mycoplasma medium and its like. However, homogeneous preparations of MAM were obtained by the following procedure.

*M. arthritidis* PG-6 was obtained from the American Type Culture Collection (Rockville, Md.; accession number 19611). Strain PG-6 produces higher levels of MAM than most other strains that have been tested. Inocula consisted of deep-frozen 1 ml aliquots of exponentially growing *M. arthritidis* PG-6. PG-6 was grown under microaerophilic condition in very gently swirled "boiled medium" (2 liters in each of two 4–6 liter Erlenmeyer flasks) at 37° C.

"Boiled medium" is an optically clear supernatant of autoclaved Edward-Hayflick medium, L. Hayflick, 23 *Tex. Rep. Biol. Med. Supp.*(1) 285 (1965), amended with N-(2-hydroxyethyl)piperzaine-N'-(2-ethanesulfonic acid) (HEPES), arginine.HCl, and penicillin G, C. Atkin et al., 137 *J. Immunol.* 1581 (1986). A batch of 4 l finished medium is made as follows. The following ingredients are mixed together in a 10 l stainless steel beaker: 4250 ml ultrapure water; 750 ml non-heat-treated horse serum (HyClone Labs, Logan, Utah) (final concentration, 15% v/v); 84 g "Bacto" PPLO Broth without Crystal Violet (Difco Lab., Detroit, Mich.) (final concentration, 2.1% w/v); and 62.5 g Fleischmann's dry baker's yeast (final concentration of 1.25% w/v). The beaker of mixture is then covered with aluminum foil and autoclaved for 40 minutes at 15 psi (132° C.). With occasional and very gentle stirring, the beaker of now custard-like mixture is chilled in a well-stirred ice bath, then left to stand overnight on ice. The mixture is then centrifuged at 4° C. for 30 minutes at about 11,000 relative centrifugal force (RCF) without braking. The essentially optically clear supernatant solution (4 l) is decanted through cheesecloth sheets and the residue is discarded. Manipulations to this point preclude maintenance of asepsis; these steps, however, effect denaturation, precipitation, and removal of most interfering macromolecules. Next, HEPES and arginine.HCl are added to 1.0% (w/v) and 0.5% (w/v), respectively, and the solution is then titrated to pH 7.0 by dropwise addition of ≦5 ml concentrated aqueous NaOH. The solution is then sterilized by autoclaving for 15 minutes at 132° C. and 15 psi. After it has cooled, penicillin G is added to 1000 U/ml. Attaining sufficient optical clarity of the medium may require supplementation or replacement of the second autoclaving step by pressure aseptic ultrafiltration on large-diameter 0.22 μm MF filters (Millipore Corp., Bedford, Mass.).

Growth of the organisms is monitored turbidimetrically until a maximum ($A_{600}$≈0.2/cm) is reached in about 52 hours, then purification steps are performed as rapidly as possible. The whole warm culture is measured for volume, and is then brought to 50% saturation with respect to $(NH_4)_2SO_4$ by addition and dissolution of crushed high-purity $(NH_4)_2SO_4$ (313 g/l according to saturation tables in A. Green & W. Hughes, 1 *Methods Enzymol.* 67 (1955)). The pH is then adjusted to 7–8 by dropwise titration with concentrated aqueous ammonia. The mixture is then centrifuged at 4° C. for 30 minutes at about 11,000 RCF without braking. The supernatant is recovered and the pellet of salted-out components is discarded. The measured volume of supernatant is similarly brought to 80% saturation with respect to $(NH_4)_2SO_4$, the pH adjusted as described above, and then the mixture is centrifuged as before. This time the pellet is saved and the supernatant is discarded. The pellet is back-extracted by addition of water to a total volume of 60 ml (calculated to give about a 1M $(NH_4)_2SO_4$ solution of appropriate volume for the first chromatographic step). Insoluble residue is then sedimented and discarded.

The MAN-containing extract solution is then subjected to gel filtration chromatography on a 2 liter column (diameter:height=1:5–10) of medium grade Sephadex G-50 (Pharmacia-LKB) equilibrated with a very high ionic strength, slightly alkaline buffer, such as 10 mM Tris.HCl, pH 8.3, 1M $(NH_4)_2SO_4$ (Buffer 1). Medium grade Sephadex G-50 is composed of dextran cross linked with epichlorohydrin as beads with wet diameters of 100–300 μm, with porosity adjusted for resolution of globular proteins of nominal molecular weights of 1,500 to 30,000. Saved and pooled were the MAM-containing fractions at elution volumes previously determined for carbonic anhydrase 30-kDalton molecular weight standard. Conductivity and pH of the pool were decreased to the values of Buffer 2 (10 mM potassium phosphate, pH 7.2) by dialysis or by repeated dilution with Buffer 2 and centrifugal ultrafiltration and concentration-ultrafiltration in Centriprep-10 tubes (Amicon, Danvers, Mass.).

The MAM-containing fraction is then adsorbed onto a 30 ml (diameter:length=1:5–10) column of Fast Flow Sepharose-S cation exchange resin (a sulfonated and proprietary cross linked agarose as mean-diameter 90 μm beads; Pharmacia-LKB) that had already been equilibrated with Buffer 2. The column is then washed with more Buffer 2 until $A_{280}$ of the effluent returns to baseline. Frontal elution of the still very impure active factor is achieved with a high salt buffer, such as 0.5M potassium phosphate, pH 7.2 (Buffer 3). One peak of 280 nm-absorbing material is eluted by this step and is saved. Electrolytes of the MAM-containing fraction are equilibrated to those of Buffer 2 as before.

A second cation exchange chromatography step is then performed by adsorbing the MAM-containing fraction onto an HR 5/10 FPLC column (1 ml bed volume) of Mono-S cation exchange resin (a sulfonated proprietary hydrophilic resin as monodisperse 10 μm beads; Pharmacia-LKB), pre-equilibrated with Buffer 2. The column is washed with Buffer 2 until $A_{280}$ returns to baseline. The active factor is eluted in one or two 0.5 ml fractions amid the next 20 ml of column flow with a linear gradient to high salt, such as 40% v/v Buffer 3. Fractions (0.5 ml) are collected directly into Centricon-10 (Amicon) centrifugal ultrafiltration concentrator tubes. Fractions are selected by murine lymphocyte proliferation assay (MLPA) or using the 280-nm elution profile (FIG. 1) and assays of similar, previous runs as a guide. FIG. 1 shows elution of MAM from a Mono-S Sepharose column. The elution time and volume commenced with the start of the salt gradient. "Salt" indicates the programmed molarity of eluant potassium phosphate, pH 7.2. Salt concentration in simultaneously eluting solution would be shown by the same gradient shifted approximately 2 ml (or 2 min.) to the right. The profile of eluted protein is given by the $A_{280}$/cm curve. Specific mitogenic activity (S.A.) of 0.5-ml fractions is shown in terms of (U/ml)+($A_{280}$/cm) or, approximately, U/(mg protein). The bulk of mitogenic activity eluted in fractions 6–8 in this example. Chromatographic runs vary sufficiently that fractions must usually be assayed for mitogen rather than simply chosen from the $A_{280}$ profile.

Selected fractions from the second cation exchange are typically about 10% pure MAM and suffice for many biological experiments, especially after ultrafiltration to remove high salt and addition of stabilizing carrier proteins such as pyrogen- and mitogen-free bovine serum albumin, or murine or human serum.

Figure 2:
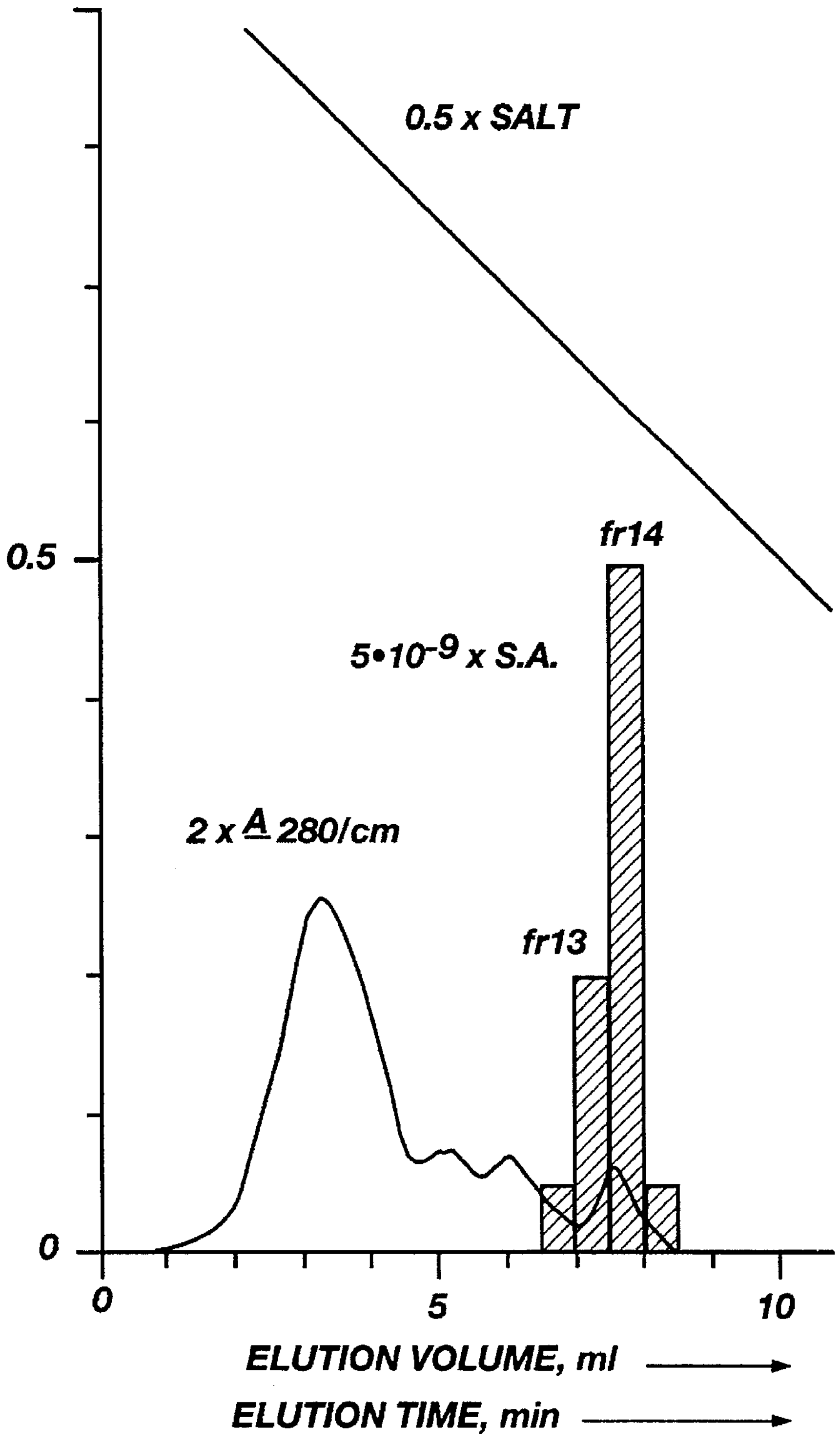
FIG. 2 shows an elution profile from the hydrophobic interaction chromatography step of MAM purification on alkyl-Superose and the specific activity of the fractions.

For the final purification step of obtaining homogeneous MAM, selected fractions are not manipulated except to add solid $(NH_4)_2SO_4$ to bring the salt concentration to 2 molar. These fractions are applied as rapidly as possible to an HR 5/10 FPLC column (1 ml bed volume) of Alkyl-Superose hydrophobic interaction resin (a proprietarily cross linked, proprietarily neopentyl-derivatized agarose as monodisperse 10 μm beads; Pharmacia-LKB) with starting conditions of 2M $(NH_4)_2SO_4$, 50 mM potassium phosphate, pH 7.2 (Buffer 4). After washing with this buffer until the $A_{280}$ returns to baseline, a linear reverse gradient is made over the next 20 ml of eluant to 50 mM potassium phosphate, pH 7.2 (Buffer 5). Simultaneous monitoring of the effluent at 214 and 280 nm shows several bands of eluted contaminant proteins that are followed by a final, discrete and weak absorbance band (FIG. 2) that typically contains about 25 μg of homogeneous MAM (see next paragraph) in about 1 ml of 50 mM potassium phosphate with roughly 1.4M $(NH_4)_2SO_4$, pH 7.2. FIG. 2 shows elution of MAM from an alkyl Superose column for the same MAM preparation shown in FIG. 1. The dimensions of the figure are the same as for FIG. 1, except "Salt" indicates the molarity (throughout a 2M to 0M gradient) of $(NH_4)_2SO_4$ in 50 mM potassium phosphate buffer, pH 7.2. Table 1 characterizes the purification scheme by overall changes wrought on MAM-containing fractions. Most surfaces will adsorb or denature purified MAM while glass will destroy it. Thus, the active fractions should be collected directly into Centricon-10 (Amicon) tubes to allow subsequent removal of salt or change of buffer.

TABLE 1

Purification of extracellular MAM.

| Fraction | Volume (ml) | Protein (mg/ml) | Mitogen (U/ml) | Mitogen Yield (%) | Specific Mitogenic Activity (U/mg) | Net Fold Purification |
|---|---|---|---|---|---|---|
| | | | Preparation No. 69 | | | |
| Whole culture[a] | 4000 | 17.2 | $2.1 \times 10^3$ | 100 | $1.2 \times 10^2$ | 1 |
| Alkyl Superose 12 | 0.5 | 0.015 | $0.2 \times 10^6$ | 1 | $0.1 \times 10^8$ | $0.1 \times 10^6$ |
| 13 | 0.5 | 0.030 | $1.1 \times 10^6$ | 7 | $0.4 \times 10^8$ | $0.3 \times 10^6$ |
| 14 | 0.5 | 0.020 | $1.9 \times 10^6$ | 12 | $1.0 \times 10^8$ | $0.8 \times 10^6$ |
| 15 | 0.5 | 0.010 | $0.1 \times 10^6$ | 1 | $0.1 \times 10^8$ | $0.1 \times 10^6$ |
| | | | Preparation No. 70 | | | |
| Whole culture[a] | 4000 | 17.4 | $2.9 \times 10^3$ | 100 | $1.7 \times 10^2$ | 1 |
| 10 | 0.5 | 0.010 | $0.6 \times 10^6$ | 3 | $0.6 \times 10^8$ | $0.4 \times 10^6$ |
| 11 | 0.5 | 0.008 | $2.5 \times 10^6$ | 11 | $3.2 \times 10^8$ | $1.9 \times 10^6$ |
| | | | Preparation No. 71/72 | | | |
| Whole culture[a] | 8300 | 14.5 | $1.0 \times 10^4$ | 100 | $7.1 \times 10^2$ | 1 |
| 10 | 0.5 | 0.035 | $0.2 \times 10^6$ | 0.1 | $0.1 \times 10^8$ | $0.7 \times 10^4$ |
| 11 | 0.5 | 0.026 | $2.0 \times 10^7$ | 11 | $7.6 \times 10^8$ | $1.1 \times 10^6$ |
| 12 | 0.5 | 0.020 | $1.8 \times 10^7$ | 11 | $9.2 \times 10^8$ | $1.3 \times 10^6$ |
| 13 | 0.5 | 0.014 | $0.4 \times 10^7$ | 2 | $2.5 \times 10^8$ | $0.4 \times 10^6$ |

[a]Assays of protein (280 nm absorbance) and of mitogenicity (lymphocyte proliferation) of starting material were actually performed on ultrafiltered culture supernatants. As for the remainder of the scheme, cellular debris was removed with the first step of 50%-saturated ammonium sulfate precipitation.

Figure 3:
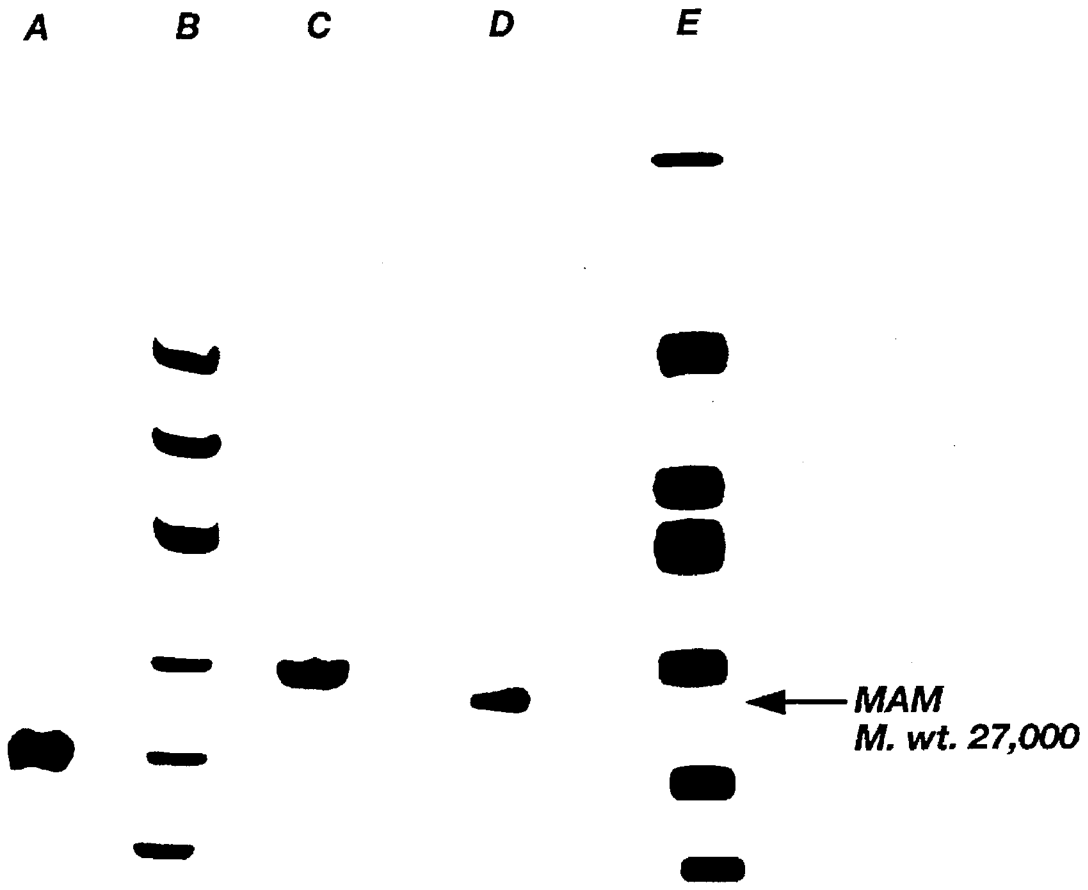
FIG. 3 shows a representation of an SDS-gradient polyacrylamide gel showing the homogeneity of MAM.

FIG. 3 shows homogeneity of MAM in the ultimate chromatographic fraction according to SDS-polyacrylamide gradient gel electrophoresis. Electrophoresis, staining, and other procedures were performed on Pharmacia-LKB PAA 4/30 precast gels according to P. Lambin et al., 74 *Anal. Biochem.* 567 (1976). Left to right, the lanes contained: 20 μg horse heart cytochrome c (Sigma Chemical, St. Louis, Mo.); 1 μg each of Bio-Rad (Hercules, Calif.) standard proteins; 5 μg bovine erythrocyte carbonic anhydrase (Sigma); 60 μl of final hydrophobic interaction chromatographic fraction 14, preparation 69, containing about 1 μg MAM; and 3 μg each of Pharmacia-LKB standard proteins. Homogeneity was similarly demonstrated (but not shown here) in the familiar non-gradient SDS-polyacrylamide gel electrophoretic system of U. Laemmli, 227 *Nature* 680 (1970). Homogeneity of this fraction was further demonstrated (but not shown here) by high and unique residue yield at each early step of amino acid sequencing by Edman degradation, described below.

The biological activity of homogeneous MAM is heat labile and protease labile. By comparison to globular molecular weight standard proteins, homogeneous MAM gave a molecular weight estimate of 27,000 Daltons in each of two gel filtration methods (on Sephadex G-50 or Superose 12, both from Pharmacia-LKB) and in two denaturing gel electrophoretic methods (described above). The molecular weight of MAM had been previously been reported to be about 15,000 as estimated by gel filtration. C. Atkin et al., 137 *J. Immunol.* 1581 (1986). The earlier method resulted in only partial (≦200-fold) purification of MAM, whereas the method reported herein results in vastly greater purification (see next paragraph) to apparent homogeneity. The reported molecular weight of MAM of 15,000 may have represented degraded but still active MAM molecules, but more likely was an artifact of delayed elution from the gel filtration resin because of MAM-resin adsorption under conditions of much lower ionic strength than used here. The apparent isoelectric point of MAM is estimated as pI>9.0 from isoelectric focusing. The essentially homogeneous MAM retains all the biological activities noted above for crude *M. arthritidis* culture supernatants, including $V_\beta$-specific proliferation of T cells, induction of interleukin-2 production, and in vivo immunosuppressive properties. Half-maximal mitogenic activity for genetically appropriate T-cells occurs at about $10^{-14}$M MAM. The specific mitogenic activity of homogeneous MAM for murine lymphocytes according to MLPA (about $1\times10^{8}$ U/mg) corresponds to about a million-fold purification of the mitogenic activity of crude culture supernatants (about 100 U/mg culture supernatant proteins).

The combination of using a high-MAM-yielding strain of *M. arthritidis*, propagating the organisms in "boiled medium," back extraction of the material that was insoluble in 80% saturated $(NH_4)_2SO_4$, and especially gel filtration at maximum ionic strength short of salting out MAM, yielded fractions that could be efficiently purified by cationic exchange chromatography. No other combination of steps has been found to yield homogeneous preparations of MAM. It is thought that these steps permit purification of homogeneous MAM because they minimize formation of intractable complexes of MAM with nucleic acids and other high molecular weight components of the starting culture.

Amino Acid Sequence of Purified MAM

The amino acid sequence of the N-terminal region of MAM, purified according to the procedure described above, was determined by a pulsed liquid phase method with a BioBreen-treated fiber glass filter sample support based on the Edman degradation method. P. Edman & G. Begg, 1 *Eur. J. Bioch.* 80 (1967); T. Hugli, *Techniques in Protein Chemistry* (1989); P. Matsudaira, *A Practical Guide to Protein and Peptide Purification for Microsequencing* (1989). The machine used was an Applied Biosystems, Inc. (ABI, Foster City, Calif.) Model 477A Protein Sequencer. Using this procedure the sequence of the N-terminal region of mature MAM protein was obtained, which is identified as SEQ ID NO:1.

Nucleotide Sequence of MAM Gene

A genomic library of *M. arthritidis* PG-6 was prepared according to standard methods in the EMBL3 phage vector. *M. arthritidis* genomic DNA was partially digested with the restriction endonuclease SalI and then ligated into SalI-digested EMBL3 vector DNA. The resulting library of clones was screened for the MAM gene by Southern hybridization (or "Southern blotting," E. Southern, 98 *J. Mol. Biol.* 503(1975); for modern elaboration of this technique see J. Sambrook et al., *Molecular Cloning* §§9.31–9.59 (2d ed., 1989)) with the 5'-$^{32}$P-phosphorylated synthetic degenerate oligodeoxynucleotide

GAAAAYCCAA AAAAAGCWCA AAAACA 26 (SEQ ID NO:2)

that was designed by reverse translation (according to the codon usage table of Muto, 23 *Israel J. Med. Sci.* 334 (1987) for *Mycoplasma capricolium*) to match as closely as possible the actual coding sequence for amino acids 6–14 of SEQ ID:NO:1. This and other oligodeoxynucleotides were synthesized using an ABI Model 380B DNA Synthesizer with proprietary phosphoramidite chemistry.

Four positive recombinant clones were selected for further characterization, clones 1246, 1410, 1722, and 1903. Southern analysis of these four indicated that a 4 kb HindIII fragment, a 3 kb BamHI fragment, and a 1.6 kb Sau3AI fragment probably contained the entire MAM gene. These restriction fragments were subcloned into $pBSSK^+$ and pTZ18R vectors as follows. Clone pBSMAM-1410-Sau3AI is a subclone of the 1.6 kb Sau3AI fragment of clone 1410 in $pBSSK11^+$. Clones pTZMAM-1722-He and pTZMAM-1722-Hn are subclones, in opposite orientations, of the 4 kb HindIII fragment of clone 1722 in pTZ18R. Nucleotide sequencing of these subclones with the Sanger dideoxynucleotide chain termination method, F. Sanger et al., 74 *Proc. Nat'l Acad. Sci. USA* 5463 (1977), yielded a sequence of the entire MAM gene, SEQ ID NO:3.

The sequenced MAM gene contains a region that, when translated, gives an amino acid sequence identical to that determined by direct amino acid sequencing (amino acids 1–54). This N-terminal region of the mature MAM protein is preceded by a 39 amino acid residue signal peptide or pre-peptide. Mature MAM (SEQ ID NO:4) contains 213 amino acid residues, which is calculated to have a molecular weight of 25,294 and a pI of 10.1.

Identification of a Peptide with Biological Activity

Figure 4B:
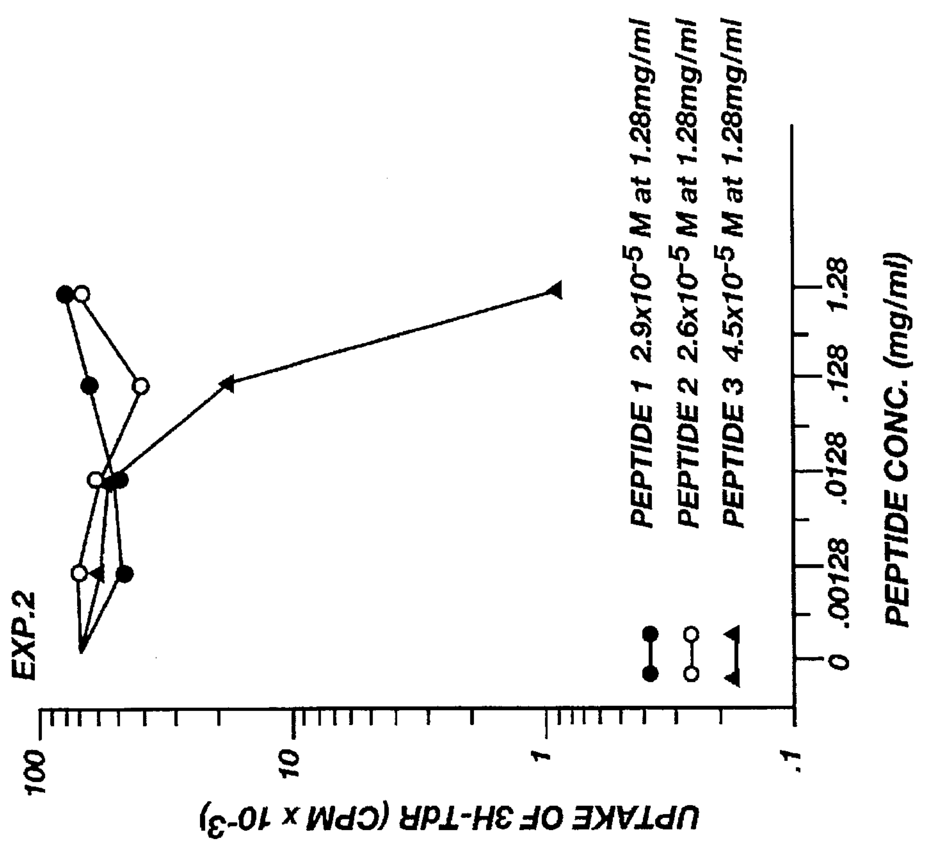
FIGS. 4A and 4B show the effects of synthetic peptides, SEQ ID NO:5, (●) SEQ ID NO:6 (○), and SEQ ID NO:7 (▲), on MAM-induced lymphocyte proliferation.
Figure 4A:
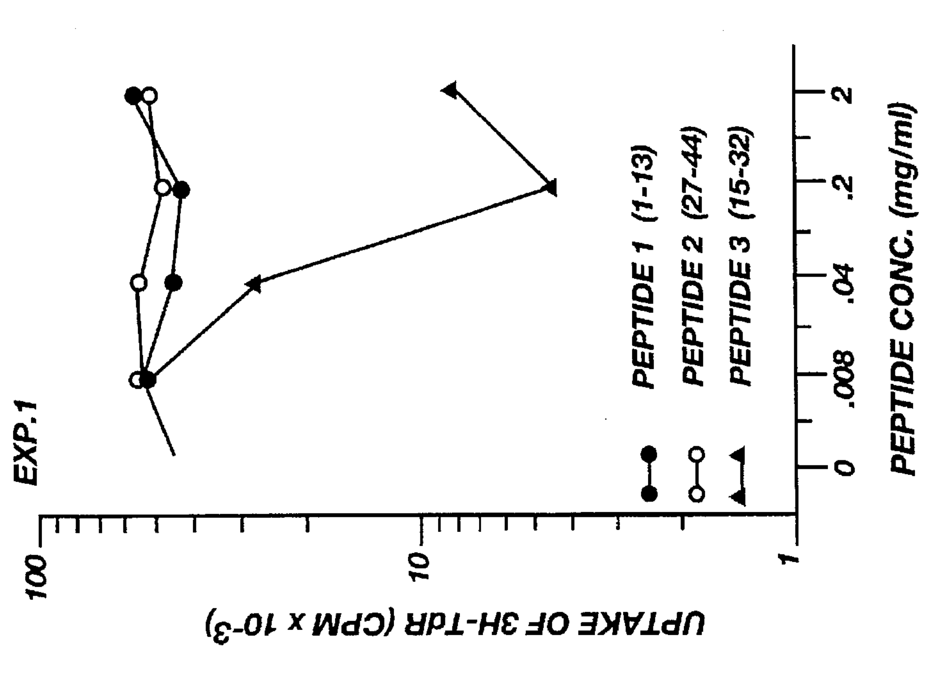
Figure 5A:
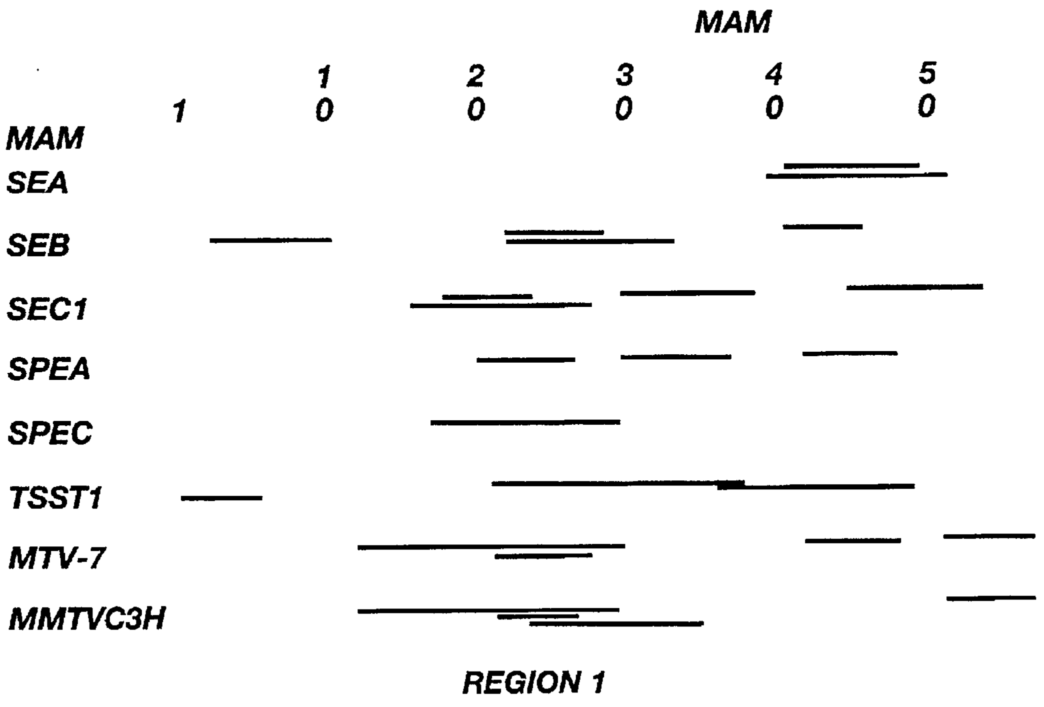
FIGS. 5A–5D show small regions of the primary sequence of MAM that resemble regions of Gram-positive bacterial and retroviral superantigens.
Figure 5B:
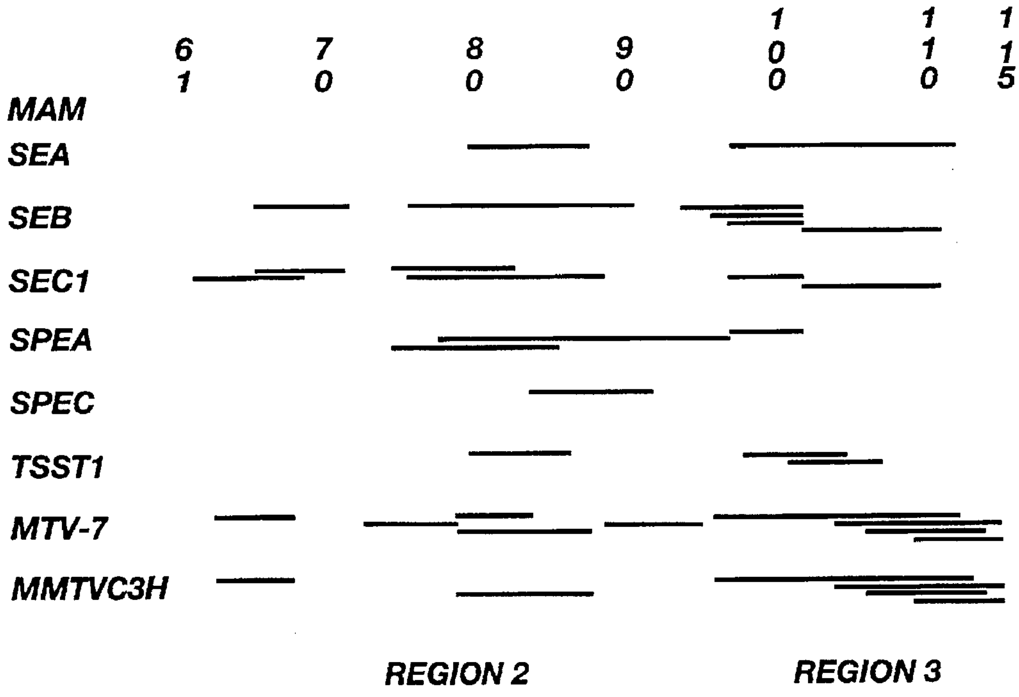
Figure 5C:
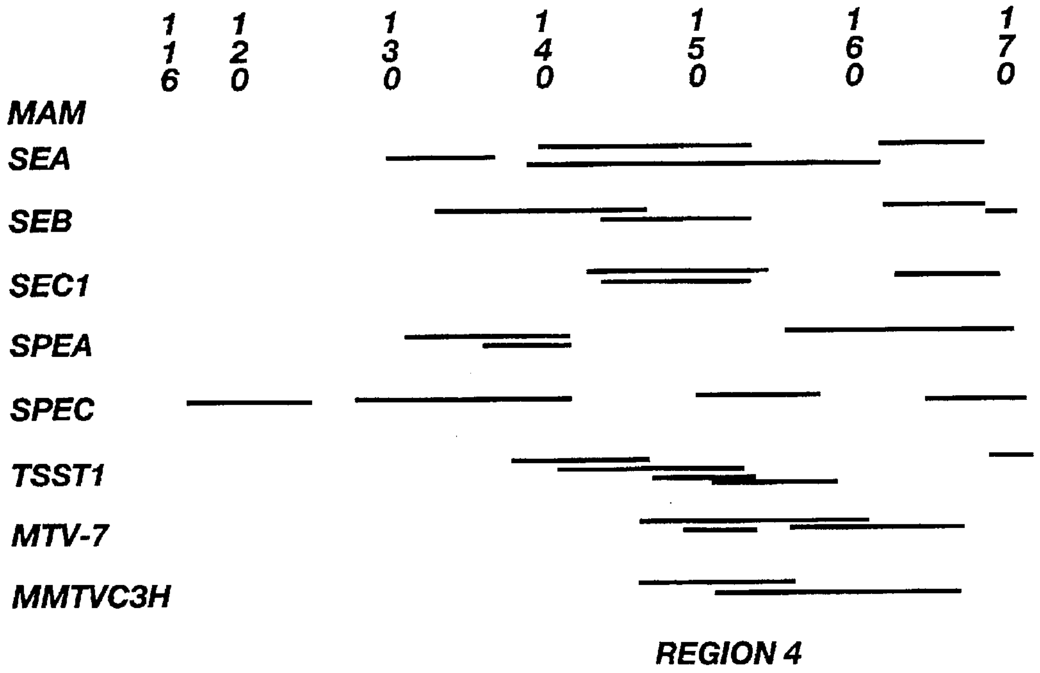
Figure 5D:
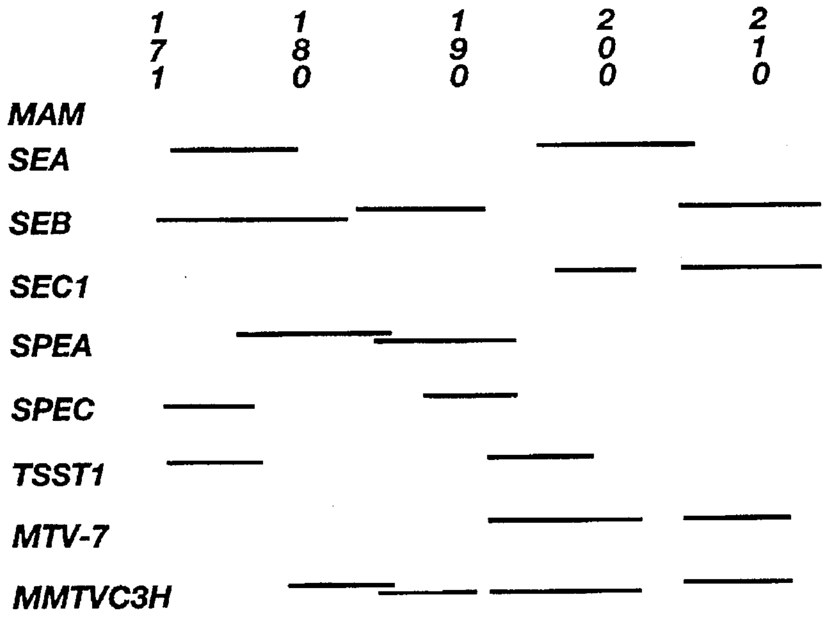

To confirm that the amino acid sequence determined by N-terminal sequencing of the homogeneous protein preparation was the sequence of a protein having MAM activity, three peptides were synthesized and tested for ability to block the mitogenic activity of intact MAM protein by competitive inhibition. The peptides chosen were SEQ ID NO:5, SEQ ID NO:6, and SEQ ID NO:7 which include, respectively, amino acids 1–13, 27–44, and 15–32 of mature MAM. These and other peptides were synthesized on an ABI Model 431A Peptide Synthesizer using proprietary Fmoc-based modified Merrifield technique. In trials, each of the peptides was pre-incubated with genetically responsive murine splenocytes for 1 hour prior to the addition of MAM. Lymphocyte activation was measured by a standard procedure using incorporation of tritiated thymidine ($^3$H-TdR) into replicated DNA. B. Cole, 2 *Methods in Mycoplasmol-* ogy 389 (1983). Similar results were obtained from mitogen at two concentrations: homogeneous MAM preparation 71/72, fraction 12, at 1:25,000- and 1:250,000-fold dilutions corresponded to approximate MAM concentrations of 0.8 ng/ml and 0.8 pg/ml, or 30 pM and 30 fM, respectively. As shown in FIG. 4, SEQ ID NO:7 was inhibitory for MAM-induced proliferation whereas SEQ ID NO:5 and SEQ ID NO:6 were not. This result strongly suggests that the N-terminal sequence is indeed that of MAM and not of a contaminant. Further, amino acids 15–32 appear to comprise a domain of mature MAM that has a biological activity. Fragments of SEQ ID NO:7 can also inhibit MAM-induced cell proliferation. Such fragments can be identified and prepared according to methods known in the art. None of the peptides had any effect on concanavalin A-induced lymphocyte stimulation.

These results further suggest that if MAM or MAM-like amino acid sequences present in other superantigens are responsible for triggering or causing the flares in commonly seen human autoimmune diseases, then therapeutic interventions may be developed. One such therapeutic intervention would comprise administering synthesized peptides corresponding to these active domains of the superantigen to competitively block lymphocyte activation by the intact superantigen. Another therapeutic intervention would comprise immunizing individuals against intact superantigens or against those superantigen domains that are active in initiation of the disease process. Immunization or treatment of patients with peptides, selected for their regions of sequence similarity between MAM and other superantigens—even if not directly involved in lymphocyte activation, may induce an immune response to the superantigen that blocks all of its biological activities.

Sequence Comparisons of MAM to other Superantigens

The amino acid sequence of MAM, as deduced by direct amino acid sequencing of the N-terminal region of MAM (SEQ ID NO:1) together with deducing the entire amino acid sequence of MAM from the nucleotide sequence of the MAM gene (SEQ ID NO:4), was compared to amino acid sequences of other superantigens. The purpose of these comparisons was to identify oligopeptide segments that are homologous between MAM and these other superantigens. The rationale is that the presence of homologous oligopeptide segments may reflect similar functionalities or binding sites within this structurally diverse group of proteins. The nature of the analysis does not require overall sequence similarity. Any sequential ordering of similar oligopeptide segments may be detected in the MAM-superantigen being compared.

Sequence comparisons were made by computer using the DDMATRIX program obtained from Intelligenetics (Mountain View, Calif.). MAM to superantigen comparisons were made by comparison of all possible 23-mer or 24-mer combinations. Rather than search for exact identities of amino acid sequence segments, conservative substitutions of amino acid residues were permitted according to the scheme of M. Jimenez-Montano & L. Zamora-Cortina, *Evolutionary model for the generation of amino acid Sequences and its application to the study of mammal alpha-hemoglobin chains*, Proc. VIIth Int'l Biophysics Congress, Mexico City (1981). Conservative substitution groups are shown in the following table.

TABLE 2

| Residue or Group | Physical Character |
|---|---|
| Pro | Proline |
| Ala, Gly | Minimal side chains, either hydrophobic or hydrophilic |
| Ser, Thr | R—OH side chains, hydrophilic |
| Asn, Gln | Amide side chains, hydrophilic |
| Asp, Glu | Carboxylic acid side chains, hydrophilic |
| His | Histidine, basic |
| Lys, Arg | Alkyl amine side chains, basic |
| Cys | Cysteine |
| Ile, Leu, Met, Val | Hydrophobic alkyl side chains |
| Phe, Trp, Tyr | Aromatic |

The amino acid sequence of MAM was compared to the following bacterial superantigen amino acid sequences: toxic shock syndrome toxin 1 (TSST-1, GenBank accession number J02615, D. A. Blomster-Hautamaa et al., 261 *J. Biol. Chem.* 15783 (1986)); staphylococcal enterotoxin A (SEA, GenBank accession number M18970,M. J. Betley and J. J. Mekalonos, 170 *J. Bacteriol.* 34 (1988)); staphylococcal enterotoxin B (SEB, GenBank accession number M11118, C. L. Jones and S. A. Khan, 166 *J. Bacteriol.* 29 (1986)); staphylococcal enterotoxin C1 (SEC1, GenBank accession number X05815, G. A. Bohach and P.M. Schlievert, 209 *Mol. Gen. Genet.* 15 (1987)); streptococcal pyrogenic exotoxin A (SPEA, GenBank accession numbers SP156SPEA etc. for allele 1, SP250SPEA etc. for allele 2, SP158SPEA etc. for allele 3, and SP262SPEA for allele 4, K. Nelson et al., 174 *J. Exp. Med.* 1271 (1991)); and streptococcal pyrogenic exotoxin C (SPEC, GenBank accession number M35514, S.C. Goshorn and P. M. Schlievert, 56 *Infect. Immun.* 2518 (1988)).

The amino acid sequence of MAM was also compared to the amino acid sequences of retroviral superantigens, including: murine tumor minor lymphocyte-stimulating (Mls) antigens MTV7 (GenBank accession no. M90535, U. Beutner et al., 89 *Proc. Natl. Acad Sci. USA* 5432 (1992)), MTV1, MTV9, MTV8, MTV11, MMTV C3H, MMTV BR6, and MMTV GR (Beutner, supra); HIV-1 envelope polyprotein (GenBank accession no. M15896, A. Srinivasan et al., 5 *AIDS Res. Hum. Retroviruses* 121–129 (1989)); and HIV-1 GAG protein (GenBank accession no. M17451, B. R. Starcich et al., 45 *Cell* 637–648 (1986)). The results of these comparisons are summarized in FIGS. 5–7. In FIG. 5, solid lines indicate small regions of the amino acid sequence of MAM (SEQ ID NO:4) that resemble regions of Gram-positive bacterial and retroviral superantigens. These superantigens were considered to share a potential epitope with MAM when, allowing for conservative substitutions of amino acid residues (according to the scheme of Jimenez-Montano & Zamora-Cortina, supra), each protein being compared had at least a common tetrapeptide sequence with additional common residues separated by no more than three dissimilar amino acids. In FIG. 6, sequence similarities of Gram positive bacterial superantigens to potential epitopic "Region 1" of MAM are shown. The boxed portion of SEQ ID NO:8 corresponds to the oligopeptide able to block lymphocyte proliferation, SEQ ID NO:7. Other boxed amino acids in SEQ ID NO:9 through SEQ ID NO:14 show regions of conservative amino acid similarity. These results show that there are numerous examples of conservative amino acid sequence similarities between MAM and other superantigens. Some of these similarities may not have biological significance. However, it is noteworthy that with allowance of conservative residue substitutions and minimal gaps and insertions, the 17-residue motif of MAM(16–32) and of SEQ ID NO:15, Val Gln Asn Leu Asn Asn Val Val Phe Thr Asn Lys Glu Leu Glu Asp Ile, is segmentally but strongly represented in both bacterial and (see next section) murine retroviral antigens. It is further noteworthy that this SEQ ID NO:15, embodied as all but the first and last residues of synthetic peptide SEQ ID NO:7, was shown to be capable of inhibiting MAM-induced cell proliferation (FIG. 4). This result suggests that sequence comparisons may be beneficial in selecting candidate peptides for blocking or immunizing against superantigens responsible for human autoimmune disease.

Sequence Comparisons of MAM to Human Immunodeficiency Virus (HIV)

Retroviruses have been postulated to play a role in human rheumatic diseases. Further, antibodies to human T-cell leukemia virus 1 (HTLV-1) and to human immunodeficiency virus 1 (HIV-1) have been detected in sera from patients with lupus and autoimmune diseases. Since lupus patients did not harbor HIV nucleic acid, it is likely that the antibodies that were detected were directed to an agent that bears antigenic components similar to some components of HIV.

Superantigens may play a role in AIDS. HIV, the causal agent of AIDS, can only replicate in activated lymphocytes. Superantigens activate T lymphocytes, thereby providing the virus more cells in which it can multiply. Evidence for the existence of a superantigen in HIV is that HIV replicates better in T cells expressing the $V_\beta 12$ and $V_\beta 17$ human T cell receptors than it does in other T cell subsets. J. Laurence et al., 358 *Nature* 255 (1992). Importantly, human $V_\beta 12$ and $V_\beta 17$ are among the subsets that are activated by MAM, and are equivalent to the murine $V_\beta 8$ and $V_\beta 6$ T cell receptors.

Sequence comparisons of MAM with known sequences of HIV proteins reveal the existence of a number of similar regions, FIG. 7. In FIG. 7, sequence similarities of retroviral superantigens and HIV-1 proteins to potential epitopic "Region 1" of MAM are shown. The boxed portion of SEQ ID NO:16 corresponds to the oligopeptide able to block lymphocyte proliferation, SEQ ID NO:7. Other boxed amino acids in SEQ ID NO:17 through SEQ ID NO:23 show regions of conservative amino acid similarity. Some of these regions of sequence similarity are also similar to sequence domains in the murine retroviral superantigens. Thus the motifs Val Gln Asn Leu Gln Gly Gln Met (SEQ ID NO::24) (HIV-GAG) and Val Gln Gln Gln Asn Asn Leu Leu (SEQ ID NO:25) (HIV Z321, envelope) are similar to both mouse MTV-7 retroviral superantigen (Val Gln Asp Tyr Asn Leu Asn Asn; SEQ ID NO:26) and to MAM (SEQ ID NO:15) (FIG. 7). The latter motif is duplicated in the biologically active peptide (SEQ ID NO:7) that was synthesized to correspond to amino acid residues 15 to 32 of MAM. Comparison of MAM sequences to those of HIV may therefore detect the existence of HIV superantigens.

Thus, if regions of sequence similarity between MAM and HIV, HTLV-1, or other viruses are regions important in inducing immunodysfunction, then protective strategies may be used against the potential harmful effects of these superantigens. Such protective strategies include immunizing the host with peptides that include these sequences or administering peptides that bear these sequences.

Sequence Comparisons of MAM to Other Proteins

Sequence similarities have also been detected between MAM and a number of other proteins including some regulatory proteins. MAM or MAM peptides may also be used to enhance or block the action of these regulatory proteins.

Utility of the Invention

Homogeneous preparations of MAM or specific MAM peptides may be used as reagents to modify immune function in vitro and in vivo as exemplified by the following examples.

EXAMPLE 1

MAM may be used for detecting or selecting (isolating) specific $V_\beta$-chain TCR-bearing T cells in vitro or in vivo. B. Cole et al., *Clin. Infect. Dis.* (in press, 1993); B. Cole et al., 150 *J. Immunol.* 3291 (1993); L. Baccala et al., 35 *Arthritis Rheum.* 434 (1992).

Lymph node cells were suspended at $1.25\times10^6$/ml in 2 ml 24-well plates in RPMI 1640 medium supplemented with 200 mM L-glutamine, 5% human serum, $2.5\times10^{-5}$M 2-mercaptoethanol, 0.11% sodium pyruvate, 0.1 mM nonessential amino acids (GIBCO Laboratories, Chicago Falls, Ohio), 50 U/ml penicillin G, and 50 μg/ml streptomycin sulfate. Lymphocyte cultures were incubated with MAM ($10^7$ to $5\times10^7$ U/ml) at 1:5000 for 3 to 5 days. As controls, lymphocytes were unstimulated or incubated for 3 days with 5 μg/ml concanavalin A. The cultures were then harvested, and the dead cells were removed by Ficoll gradient centrifugation.

A set of 17 riboprobes for analysis of $V_\beta^b$ haplotype mice was prepared as previously described, P. Singer et al., 170 *J. Exp. Med.* 1869 (1989), which is hereby incorporated by reference. A new set of 8 $V_\beta$ riboprobes for analysis of $V_\beta^a$ haplotype mice (strains C57BR and SWR) was also made. This $V_\beta^a$ haplotype-specific probe set lacks riboprobes for the 9 $V_\beta$ (5.1, 5.2, 8.1, 8.2, 8.3, 9, 11, 12, 13) that are genetically deleted in $V_\beta^a$ mice, and includes new $V_\beta^a$ probes for $V_\beta 1$, 3, and 6, which are polymorphic between $V_\beta^b$ and $V_\beta^a$ haplotype mice The principles of the multiprobe RNase protection assay have been detailed in P. Singer et al., 170 *J. Exp. Med.* 1869 (1989). In brief, RNA (5 to 10 μl) extracted from cell pellets and lyophilized was dissolved in hybridization buffer (5 μl of 80% formamide, 0.4M NaCl, 1 mM EDTA, and 40 mM PIPES, pH 6.7) containing the appropriate riboprobe set ($1\times10^3$ cpm×number of uridine residues in the riboprobe set). The solution was overlaid in mineral oil and incubated at 56° C. for 12 to 16 hours. Unhybridized probe and target RNA was digested with RNase A (5 μg/ml) and RNase T1 (10 U/ml) in 50 μl digestion buffer (10 mM Tris, pH 7.5, 5 mM EDTA, and 0.3M NaCl). After 1 hour at 30° C., digested samples containing the "protected" probe-target duplexes were phenol-chloroform extracted, ethanol precipitated, dissolved in sample buffer, and electrophoresed in standard 6% polyacrylamide-urea sequencing gels. Autoradiography of the dried gel was done on Kodak XRP film at −70° C. with intensifying screen for 10 to 20 hours. An Ambis radioanalytic imaging apparatus (Ambis Systems, San Diego, Calif.) was used to quantitate $V_\beta$ transcript levels. The net cpm at a given band corresponding to a specific protected $V_\beta$ probe was calculated by the formula ((cpm of $V_\beta$-specific band) —(cpm background around the band)—(number of uridine residues on the specific $V_\beta$ probe)); this value was then expressed as the percentage of the $V_\beta$ included in the probe set.

Lymph node cells from two $V_\beta^b$ haplotype strains, CBA/CaJ (H-$2^k$, Mls$^b$) and CBA/J (H-$2^k$, Mls$^{a+c}$) were grown in the presence of MAM for 3 to 5 days and viable activated cells collected over a Ficoll gradient. The results with CBA/CaJ lymphocytes (Table 3) show that MAM activates T cells bearing $V_\beta 6$, 8.1, 8.2, and 8.3. Slightly different results were obtained with cells from CBA/J mice, which show somatically imposed clonal deletions/depletions of cells bearing $V_\beta 3.1$, 5, 6, 7, 8.1, 9, 11, 12, and 16 because of the presence of various MTV integrants on several chromosomes.

TABLE 3

| | % $V_\beta$ Transcripts in | | | |
|---|---|---|---|---|
| | CBA/CaJ Cells | | CBA/J Cells | |
| $V_\beta$ Tested | Control | MAM | Control | MAM |
| 1 | 2.2 | 0.4 | 2.3 | 0.6 |
| 2 | 9.5 | 1.8 | 10.8 | 0.8 |
| 3.1 | 3.7 | 2.1 | 0.1 | 0.2 |
| 4 | 1.8 | 0.4 | 3.1 | 0.3 |
| 5.1 | 3.9 | 3.6[a] | 2.2 | 3.6 |
| 5.2 | 0.2 | 0.2 | 0.2 | 0.7 |
| 6 | 2.8 | 5.6 | 0.3 | 0.2 |
| 7 | 0.8 | 0.4 | 1.0 | 0.4 |
| 8.1 | 20.2 | 30.8 | 8.0 | 17.8 |
| 8.2 | 17.1 | 34.0 | 18.8 | 37.8 |
| 8.3 | 16.5 | 15.6 | 24.0 | 31.6 |
| 10 | 2.6 | 0.5 | 2.1 | 0.4 |
| 11 | 0.8 | 0.4 | 2.2 | 1.1 |
| 12 | 1.2 | 1.0 | 0.7 | 1.0 |
| 13 | 4.3 | 1.1 | 7.3 | 0.9 |
| 14 | 8.7 | 1.5 | 12.1 | 1.4 |
| 15 | 4.1 | 0.4 | 4.7 | 0.5 |

[a]$V_\beta$ used by MAM are underlined.

EXAMPLE 2

MAM may be used for modifying immune responses in vivo by suppressing or changing specific T or B lymphocyte functions. B. Cole & D. Wells, 58 *Infect. Immun.* 228 (1990); B. Cole et al., *Clin. Infect. Dis.* (in press, 1993).

Table 4 shows that MAM promotes survival of transplants, exemplifying MAM's ability to suppress T cell functions. Detailed methodology for skin grafting has been described in D. Steinmuller, 108 *Meth. Enzymol.* 20 (1984), which is hereby incorporated by reference. BALB/c skin grafts about 1 cm in diameter were taken from the ear and cleaned of cartilage and fat. Grafts were made onto 1 cm beds of vascular fascia of the flanks of C3H/HeJ mice. C3H mice received only two or three injections of MAM diluted 1:20 or PBS before receiving a graft from a BALB/c mouse. Mice that received two (experiment 2) or three (experiment 3) injections of MAM showed a significant prolongation of graft survival as compared with the survival of mice that received PBS.

TABLE 4

| Material injected into C3H recipient | Survival of BALB/c skin (days)[a] | Significance |
|---|---|---|
| Experiment 1 | | |
| PBS × 1 | 8.6 ± 1.3 | NS[b] |
| MAM × 1 | 10.0 ± 1.6 | |
| Experiment 2 | | |
| PBS × 2 | 9.7 ± 1.8 | P < 0.05 |
| MAM × 2 | 12 ± 1.5 | |
| Experiment 3 | | |
| PBS × 3 | 10.3 ± 0.6 | P < 0.05 |
| MAM × 3 | 14.6 ± 2.7 | |

[a]Values are the means for six mice per group ± SD.
[b]Not significant.

Table 5 shows the effects of MAM on humoral antibody responses to ovalbumin (OVA) as measured in terms of lymphocyte proliferation, exemplifying enhancement of B cell functions of MAM in vivo. The method used for stimulation of lymphocytes is detailed in B. Cole et al., 144 *J. Immunol.* 425 (1990), which is hereby incorporated by reference. Proliferative responses of lymphocytes to OVA were measured by a modification of the referenced lymphocyte proliferation assay. CBA or C3H mice were injected in the rear footpads with 50 μg of OVA emulsified with complete Freund's adjuvant. After 12 days, draining lymph nodes were harvested and lymphocytes were tested for proliferative responses to OVA with use of RPMI 1640 medium supplemented with 2 mM L-glutamine, 5% heat-inactivated human serum, $5\times10^{-5}$M 2-mercaptoethanol, 0.011% sodium pyruvate, 1% nonessential amino acids (×100), penicillin, and streptomycin.

TABLE 5

| | | Specific uptake of [$^3$H] thymidine (cpm × $10^3$)[a] in response to OVA at indicated concentration (μg/ml)[b] | | | |
|---|---|---|---|---|---|
| Injection schedule | | Experiment 1 | | Experiment 2 | |
| Day 0 | Day 2 | 50 | 250 | 50 | 250 |
| PBS | OVA | 5.8 | 9.0 | 1.5 | 2.1 |
| MAM 1:10 | OVA | 34.0 | 29.1 | 8.3 | 14.9 |
| PBS + OVA | — | 9.8 | 18.3 | 1.0 | 3.4 |
| MAM 1:10 + OVA | — | 27.6 | 37.7 | 5.9 | 16.8 |
| OVA | PBS | 3.0 | 3.3 | 7.0 | 10.2 |
| OVA | MAM 1:10 | 23.6 | 39.5 | 27.5 | 34.7 |

[a]Uptake of [$^3$H]thymidine in response to OVA minus uptake in absence of OVA.
[b]Values are the means for two separate mice tested in triplicate.

EXAMPLE 3

MAM may be used for triggering, enhancing, exacerbating, or otherwise altering the course of autoimmune arthritis thereby providing an experimental model system for the study of the etiology and mechanisms of development of autoimmune diseases. B. Cole & M. Griffiths, 36 *Arthritis Rheum.* 994 (1993).

Table 6 shows the effects of MAM, SEA, and SEB on the development of CIA. SEB was chosen since, as with MAM, it activates T cells bearing the $V_\beta8$ chain segments of the TCR. SEA was also used since it fails to activate any of the T cell subsets that have been shown or thought to mediate CIA (i.e., T cells bearing $V_\beta5$, 6, 7, 8, and 9). In this experiment, B10.RIII mice, a very susceptible strain (100% incidence with injection of ≦100 μg native porcine type II collagen (PII)), were suboptimally immunized with 5 μg PII. PII was prepared as previously described in M. Griffiths et al., 24 *Arthritis Rheum.* 781 (1981), which is hereby incorporated by reference. PII was dissolved overnight in 0.1N acetic acid and was then emulsified with 50% Freund's complete adjuvant. Two to four-month-old mice were immunized with 5 μg of PII emulsion intradermally in the base of the tail. The mice were challenged 16 days later with intravenous injections of 0.2 ml PBS, 1:35 MAM, or SEB or SEA (5 μg/mouse). It had previously been established that SEB and SEA in doses of 5 μg/mouse induce lymphadenopathy and splenomegaly as early as 1–2 days post-injection.

TABLE 6

| IV treatment | Arthritis incidence | Day of onset, mean ± SD | Day of maximum severity, mean ± SD |
|---|---|---|---|
| PBS, 0.2 ml | 1/10 | 5.0 | 31.0 |
| MAM 1:35, 0.2 ml | 5/10 | 8.0 ± 7.9 | 15.6 ± 7.8 |
| SEB, 5 μg | 5/10 | 8.0 ± 10.2 | 14.8 ± 9.0 |
| SEA, 5 μg | 2/10 | 14.0 ± 5.7 | 28.5 ± 3.5 |

Only one of the control animals receiving PBS developed arthritis, and the severity gradually increased until termination of the experiment at 31 days post-challenge. Mice receiving either MAM or SEB exhibited a 50% incidence of arthritis, with an early onset time. In fact, among mice treated with MAM, 3 of 10 showed arthritis just 3 days post-injection. Mean maximum arthritis severity for MAM-injected animals occurred at day 15. In contrast, SEA induced a late onset arthritis occurring in only 20% of the mice and, as in PBS-injected animals, the arthritis severity did not peak until close to termination of the experiment. Thus, these data provide evidence that MAM triggers an early onset of CIA.

We claim:

1. A homogeneous purified MAM protein having an amino acid sequence, wherein said MAM protein exhibits T-cell mitogen activity and the amino acid sequence is SEQ ID NO:4.

2. The protein of claim 1 wherein the protein is encoded by the nucleic acid sequence presented in SEQ ID:3.

3. An oligopeptide having an amino acid sequence as in SEQ ID NO:7 that inhibits MAM-induced cell proliferation.

4. The oligopeptide of claim 3 wherein the amino acid sequence is a fragment of SEQ ID NO:7.

* * * * *